(12) United States Patent
Smith et al.

(10) Patent No.: US 7,637,947 B2
(45) Date of Patent: Dec. 29, 2009

(54) ACCOMMODATING INTRAOCULAR LENS SYSTEM HAVING SPHERICAL ABERRATION COMPENSATION AND METHOD

(75) Inventors: David John Smith, Highland, CA (US); Terah Whiting Smiley, San Francisco, CA (US); John A. Scholl, San Ramon, CA (US); Denise Horrilleno Burns, Sunnyvale, CA (US); Victor Esch, Albuquerque, NM (US)

(73) Assignee: PowerVision, Inc., Belmont, CA (US)

( * ) Notice: Subject to any disclaimer, the term of this patent is extended or adjusted under 35 U.S.C. 154(b) by 430 days.

(21) Appl. No.: 11/646,913

(22) Filed: Dec. 27, 2006

(65) Prior Publication Data

US 2007/0106377 A1 May 10, 2007

Related U.S. Application Data

(63) Continuation-in-part of application No. 10/971,598, filed on Oct. 22, 2004, now Pat. No. 7,261,737, which is a continuation-in-part of application No. 10/734,514, filed on Dec. 12, 2003, now Pat. No. 7,122,053.

(60) Provisional application No. 60/433,046, filed on Dec. 12, 2002.

(51) Int. Cl.
*A61F 2/16* (2006.01)
(52) U.S. Cl. .................... 623/6.13; 623/6.23
(58) Field of Classification Search ............ 623/4.1, 623/6.11, 6.13, 6.22–6.24, 6.37, 6.39
See application file for complete search history.

(56) References Cited

U.S. PATENT DOCUMENTS 4,111,995 A 9/1978 Nelson
4,253,199 A 3/1981 Banko
4,304,895 A 12/1981 Loshaek
4,373,218 A 2/1983 Schachar
4,409,691 A 10/1983 Levy
4,435,856 A 3/1984 L'Esperance
4,490,860 A 1/1985 Rainin
4,494,254 A 1/1985 Lopez (Continued)

FOREIGN PATENT DOCUMENTS

JP 9294754 11/1997

(Continued)

OTHER PUBLICATIONS

Smiley et al.; U.S. Appl. No. 12/178,565 entitled "Lens delivery system," filed Jul. 23, 2008.

(Continued)

*Primary Examiner*—William H Matthews
(74) *Attorney, Agent, or Firm*—ShayGlenn LLP

(57) ABSTRACT

An accommodating intraocular lens includes an optic portion, a haptic portion. The optic portion of the lens includes an actuator that deflects a lens element to alter the optical power of the lens responsive to forces applied to the haptic portion of the lens by contraction of the ciliary muscles and a secondary deflection mechanism. Movement of the lens element by the actuator causes the lens element to deform and the secondary deflection mechanism causes the lens to further deform.

28 Claims, 15 Drawing Sheets

U.S. PATENT DOCUMENTS

| | | | |
|---|---|---|---|
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,615,701 A | 10/1986 | Woods |
| 4,685,921 A | 8/1987 | Peyman |
| 4,685,922 A | 8/1987 | Peyman |
| 4,693,717 A | 9/1987 | Michelson |
| 4,731,078 A | 3/1988 | Stoy et al. |
| 4,731,080 A | 3/1988 | Galin |
| 4,787,903 A | 11/1988 | Grendahl |
| 4,790,847 A | 12/1988 | Woods |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turely |
| 4,902,293 A | 2/1990 | Feaster |
| 4,932,966 A | 6/1990 | Christie et al. |
| 4,946,469 A | 8/1990 | Sarafarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 5,015,254 A | 5/1991 | Greite |
| 5,035,710 A | 7/1991 | Nakada et al. |
| 5,047,051 A | 9/1991 | Cumming |
| 5,066,301 A | 11/1991 | Wiley |
| 5,145,935 A | 9/1992 | Hayashi |
| 5,152,789 A | 10/1992 | Willis |
| 5,171,266 A | 12/1992 | Wiley et al. |
| 5,201,763 A | 4/1993 | Brady et al. |
| 5,213,579 A | 5/1993 | Yamada et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,405,386 A | 4/1995 | Rheinish et al. |
| 5,443,506 A | 8/1995 | Garbet |
| 5,444,106 A | 8/1995 | Zhou et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,665,822 A | 9/1997 | Bitler et al. |
| 5,674,282 A | 10/1997 | Cumming |
| 5,697,973 A | 12/1997 | Peyman et al. |
| 5,702,441 A | 12/1997 | Zhou |
| 5,774,273 A | 6/1998 | Bornhorst |
| 5,843,188 A | 12/1998 | McDonald |
| 5,891,931 A | 4/1999 | Leboeuf et al. |
| 5,928,282 A | 7/1999 | Nigam |
| 5,984,962 A | 11/1999 | Anello et al. |
| 6,013,101 A | 1/2000 | Israel |
| 6,015,842 A | 1/2000 | Leboeuf et al. |
| 6,117,171 A | 9/2000 | Skottum |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,388,043 B1 | 5/2002 | Langer et al. |
| 6,406,494 B1 | 6/2002 | Laguette et al. |
| 6,423,094 B1 | 7/2002 | Sarfarazi |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,503,276 B2 | 1/2003 | Lang et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,592,621 B1 | 7/2003 | Domino |
| 6,599,317 B1 | 7/2003 | Weinschenk, III et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,899,732 B2 | 5/2005 | Zadno-Azizi et al. |
| 6,926,736 B2 | 8/2005 | Peng et al. |
| 6,935,743 B2 | 8/2005 | Shadduck |
| 6,966,649 B2 | 11/2005 | Shadduck |
| 6,969,403 B2 | 11/2005 | Peng et al. |
| 7,068,439 B2 | 6/2006 | Esch |
| 7,122,053 B2 | 10/2006 | Esch |
| 7,217,288 B2 | 5/2007 | Esch et al. |
| 7,264,351 B2 | 9/2007 | Shadduck |
| 7,278,739 B2 | 10/2007 | Shadduck |
| 2001/0001836 A1 | 5/2001 | Cumming |
| 2001/0016771 A1 | 8/2001 | Cumming |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0161434 A1 | 10/2002 | Laguette et al. |
| 2002/0193876 A1 | 12/2002 | Lang et al. |
| 2003/0003295 A1 | 1/2003 | Dreher et al. |
| 2003/0018384 A1 | 1/2003 | Valyunin et al. |
| 2003/0042176 A1 | 3/2003 | Alderson et al. |
| 2003/0050695 A1 | 3/2003 | Lin et al. |

| | | | |
|---|---|---|---|
| 2003/0050696 | A1 | 3/2003 | Cumming |
| 2003/0060878 | A1 | 3/2003 | Shadduck |
| 2003/0060881 | A1 | 3/2003 | Glick et al. |
| 2003/0078656 | A1 | 4/2003 | Nguyen |
| 2003/0078657 | A1 | 4/2003 | Zadno-Azizi et al. |
| 2003/0078658 | A1 | 4/2003 | Zadno-Azizi |
| 2003/0083744 | A1 | 5/2003 | Khoury |
| 2003/0109925 | A1 | 6/2003 | Ghazizadeh et al. |
| 2003/0109926 | A1 | 6/2003 | Portney |
| 2003/0130732 | A1 | 7/2003 | Sarfarazi |
| 2003/0135272 | A1 | 7/2003 | Brady et al. |
| 2003/0149480 | A1 | 8/2003 | Shadduck |
| 2003/0158599 | A1 | 8/2003 | Brady et al. |
| 2003/0171808 | A1 | 9/2003 | Phillips |
| 2003/0187505 | A1 | 10/2003 | Liao |
| 2003/0199977 | A1 | 10/2003 | Cumming |
| 2004/0001180 | A1 | 1/2004 | Epstein |
| 2004/0006386 | A1 | 1/2004 | Valint et al. |
| 2004/0006387 | A1 | 1/2004 | Kelman |
| 2004/0008419 | A1 | 1/2004 | Schachar |
| 2004/0015236 | A1 | 1/2004 | Sarfarazi |
| 2004/0039446 | A1 | 2/2004 | McNicholas |
| 2004/0054408 | A1 | 3/2004 | Glick et al. |
| 2004/0059343 | A1 | 3/2004 | Shearer et al. |
| 2004/0082993 | A1 | 4/2004 | Woods |
| 2004/0082994 | A1 | 4/2004 | Woods et al. |
| 2004/0085511 | A1 | 5/2004 | Uno et al. |
| 2004/0111151 | A1 | 6/2004 | Paul et al. |
| 2004/0111152 | A1 | 6/2004 | Kelman |
| 2004/0111153 | A1 | 6/2004 | Woods et al. |
| 2004/0127984 | A1 | 7/2004 | Paul et al. |
| 2004/0162612 | A1 | 8/2004 | Portney et al. |
| 2004/0181279 | A1 | 9/2004 | Nun |
| 2004/0190153 | A1 | 9/2004 | Esch |
| 2005/0021139 | A1 | 1/2005 | Shadduck |
| 2005/0119740 | A1 | 6/2005 | Esch et al. |
| 2005/0149183 | A1 | 7/2005 | Shadduck |
| 2005/0165410 | A1 | 7/2005 | Zadno-Azizi et al. |
| 2005/0264756 | A1 | 12/2005 | Esch |
| 2006/0041307 | A1 | 2/2006 | Esch et al. |
| 2007/0010880 | A1 | 1/2007 | Esch |
| 2007/0088433 | A1 | 4/2007 | Esch et al. |
| 2007/0100445 | A1 | 5/2007 | Shadduck |
| 2007/0106377 | A1 | 5/2007 | Smith et al. |
| 2007/0203578 | A1 | 8/2007 | Scholl et al. |
| 2007/0213817 | A1 | 9/2007 | Esch et al. |
| 2007/0299487 | A1 | 12/2007 | Shadduck |
| 2008/0015689 | A1 | 1/2008 | Esch et al. |

FOREIGN PATENT DOCUMENTS

| | | |
|---|---|---|
| JP | 11276509 | 10/1999 |
| WO | WO 97/06751 A | 2/1997 |
| WO | WO 00/41650 A1 | 7/2000 |
| WO | WO 01/60286 A1 | 8/2001 |
| WO | WO 01/97742 A2 | 12/2001 |
| WO | WO 2004/010895 | 2/2004 |
| WO | WO 2004/046768 A2 | 6/2004 |
| WO | WO 2004/072689 A2 | 8/2004 |

OTHER PUBLICATIONS

Esch et al; U.S. Appl. No. 11/844,108 entitled "Accommodating Intraocular Lens System and Method" filed Aug. 23, 2007.

Smith et al; U.S. Appl. No. 11/844,087 entitled "Accommodating Intraocular Lens System Having Spherical Aberration Compensation and Method," filed Aug. 23, 2007.

Wyant et al; "Basic Wavefront Aberration Theory for Optical Metrology," Applied Optics and Optical Engineering, vol. XI, 1992:1-13.

Shadduck, John H.; U.S. Appl. No. 12/347,816 entitled "Intraocular lenses and business methods," filed Dec. 31, 2008.

Gruber et al.; Exhaustive soxhlet extraction for the complete removal of residual compounds . . . ; Journal of Biomedical Materials Research; vol. 53; No. 5; pp. 445-448; Mar. 2000.

Baughman et al., "Negative poisson's ratios for extreme states fo matter," Science, vol. 288, pp. 1028-2022, Jun. 16, 2000.

Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.

Jeon et al., "Shape memory and nonstructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2899, Mar. 26, 2001.

Lakes, "Lateral deformations in extreme matter," Science, vol. 288, pp. 1976, Jun. 2000.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

Mather et al., "Strain recovery in POSS hybrid thermoplastics," Polymer Preprints, vol. 41, No. 1, pp. 528-529, 2000.

Lakes et al., "Microbuckling instability in elastomeric cellular sollids," J. Materials Science, vol. 28, pp. 4667-4672, 1993.

Takahashi et al., "Structure and properties of shape-memory polyurethane block copolymers," Journal of Applied Polymer Science, vol. 60, pp. 1061-1069, 1996.

Tobushi et al., "Thermomechanical properties of shape memory polymers of polyurethane series and their applications," Journal de Physique IV, Colloque C1, vol. 6, pp. 377-384, 1996.

Xu et al., "Basic negative poisson's ratio microstructures by soft lithography," Advanced Materials, vol. 11, No. 14, 1999, pp. 1186-1189, 1999.

Your, Jingjong; U.S. Appl. No. 12/034,942 entitled "Polymeric materials suitable for ophthalmic devices and methods of manufacture," filed Feb. 21, 2008.

Your, Jingjong; U.S. Appl. No. 12/177,720 entitled "Lens material and methods of curing with UV light," filed Jul. 22, 2008.

Smiley et al.; U.S. Appl. No. 12/177,857 entitled "Accommodating intraocular lenses and methods of use," filed Jul. 22, 2008.

Smiley et al.; U.S. Appl. No. 12/178,304 entitled "Post-implant accommodating lens modification," filed Jul. 23, 2008.

Smiley et al.; U.S. Appl. No. 12/17,565 entitled "Lens delivery system," filed Jul. 23, 2008.

Choi et al.; U.S. Appl. No. 12/178,454 entitled "Systems and methods for testing intraocular lenses," filed Jul. 23, 2008.

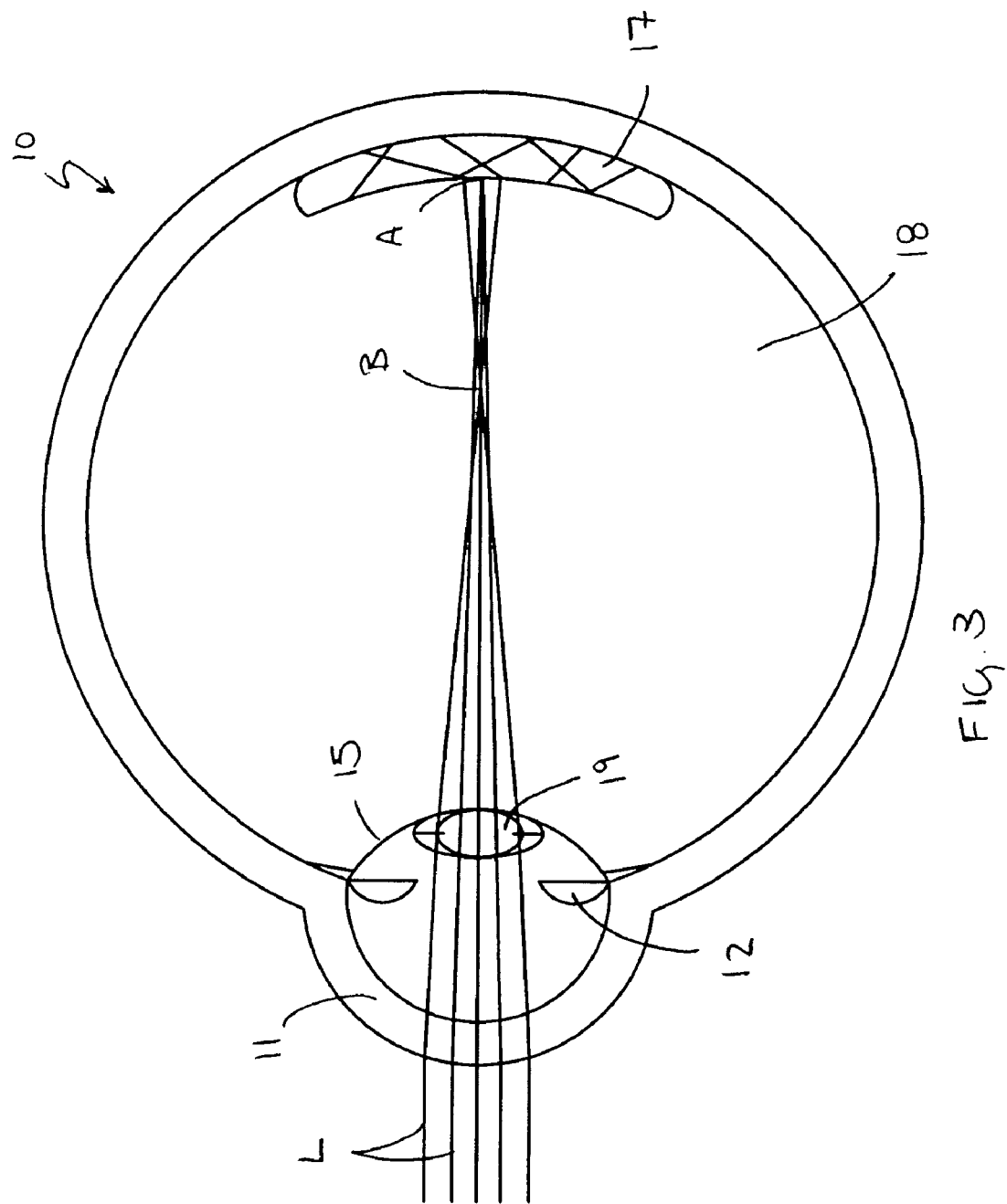

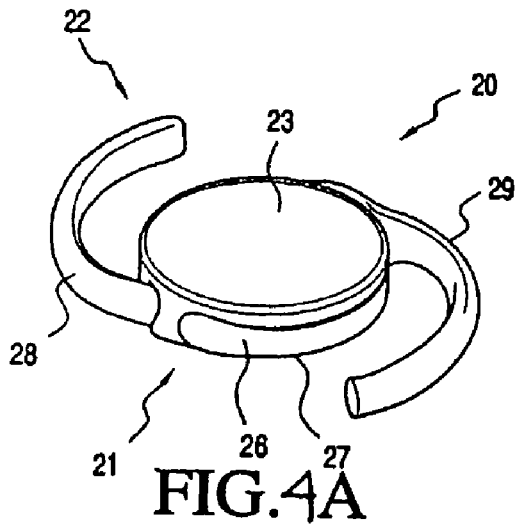
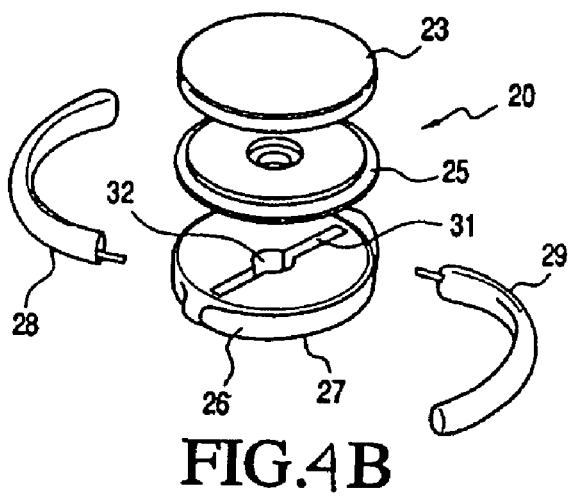
FIG.4A  FIG.4B
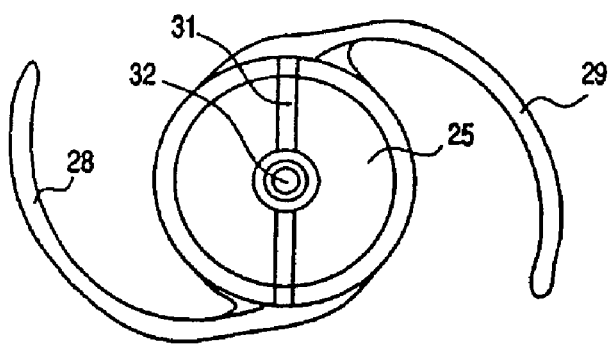
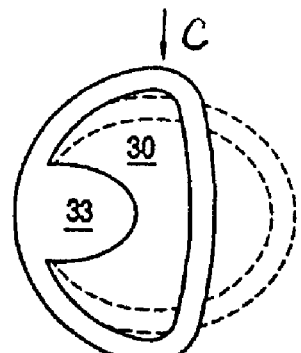
FIG.4C  FIG.5
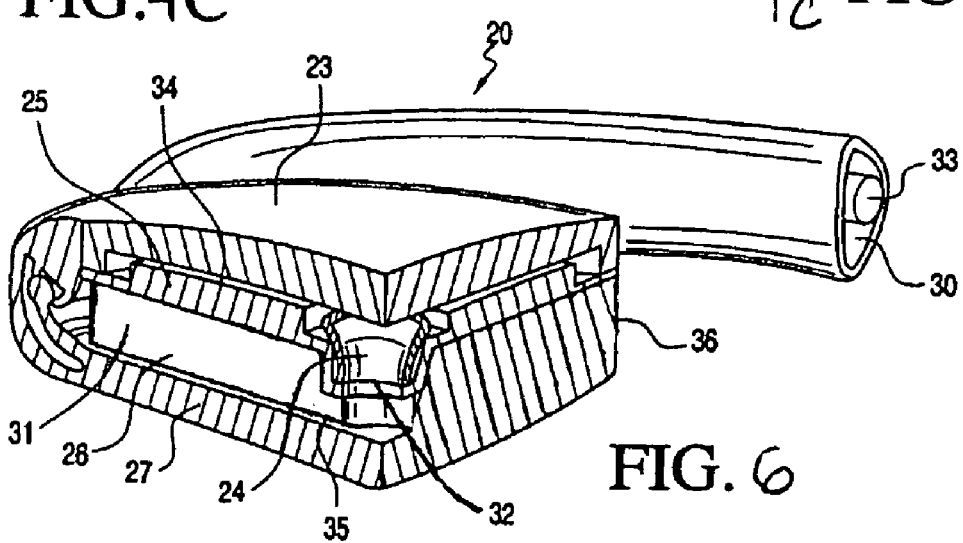
FIG.6

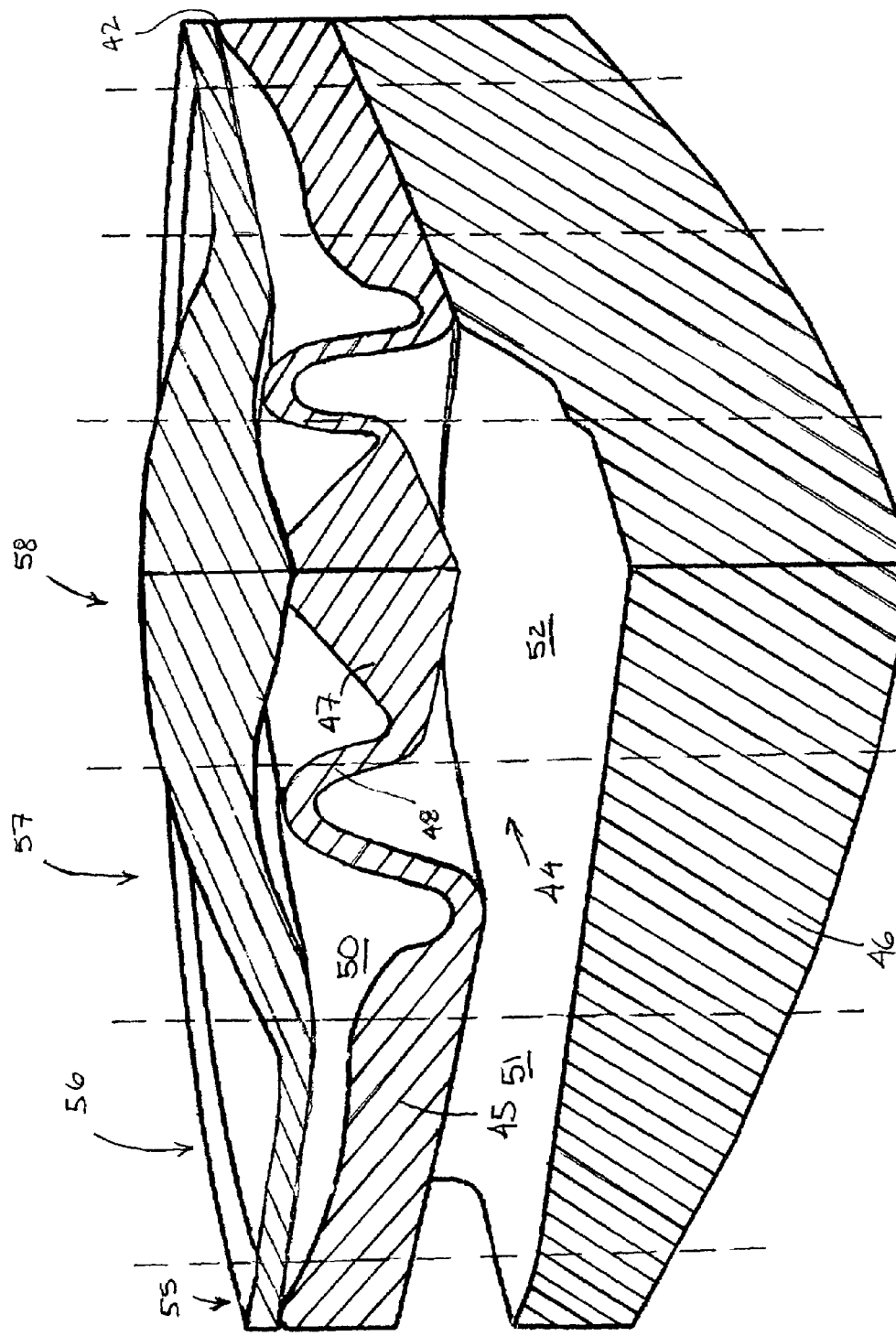

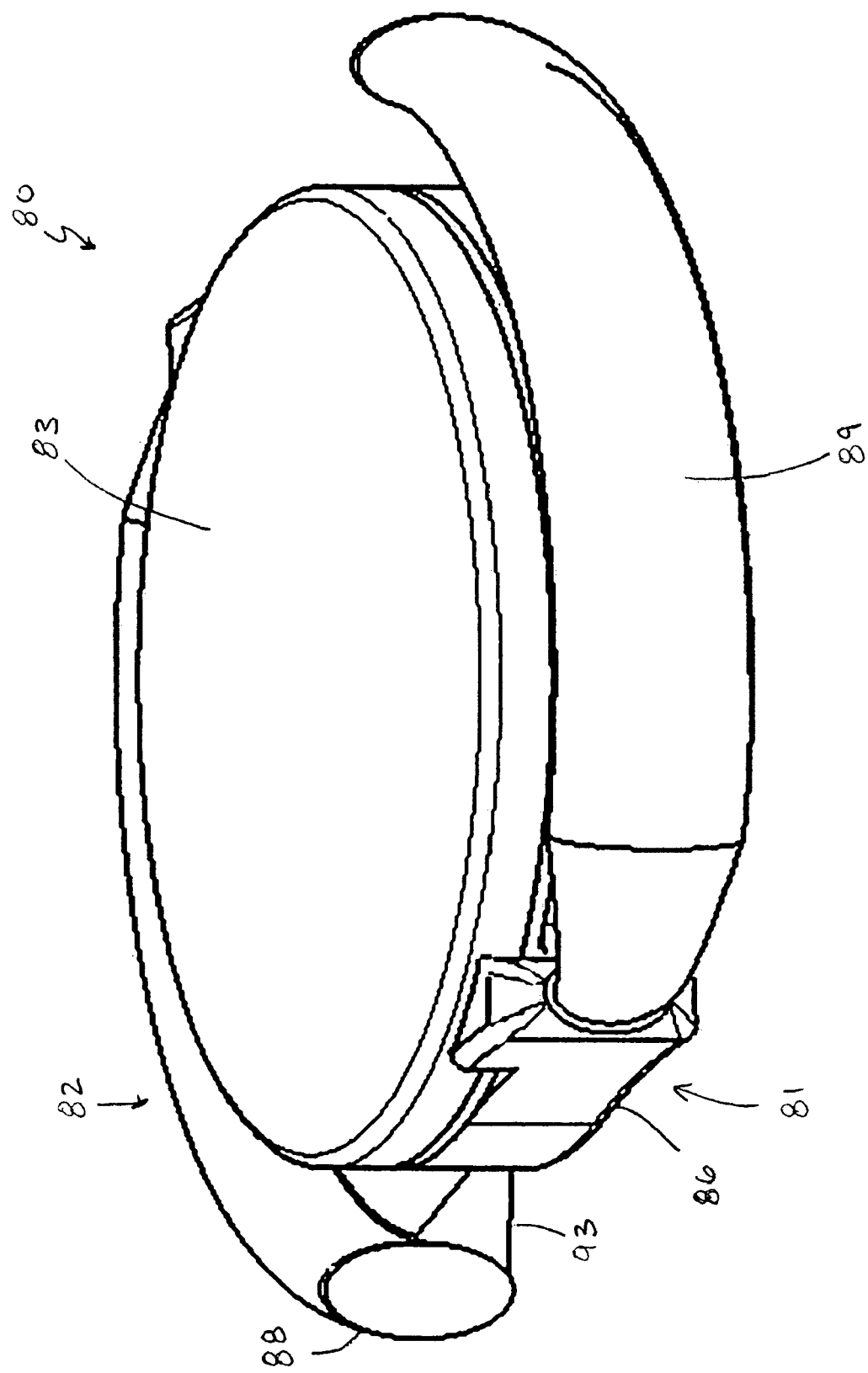

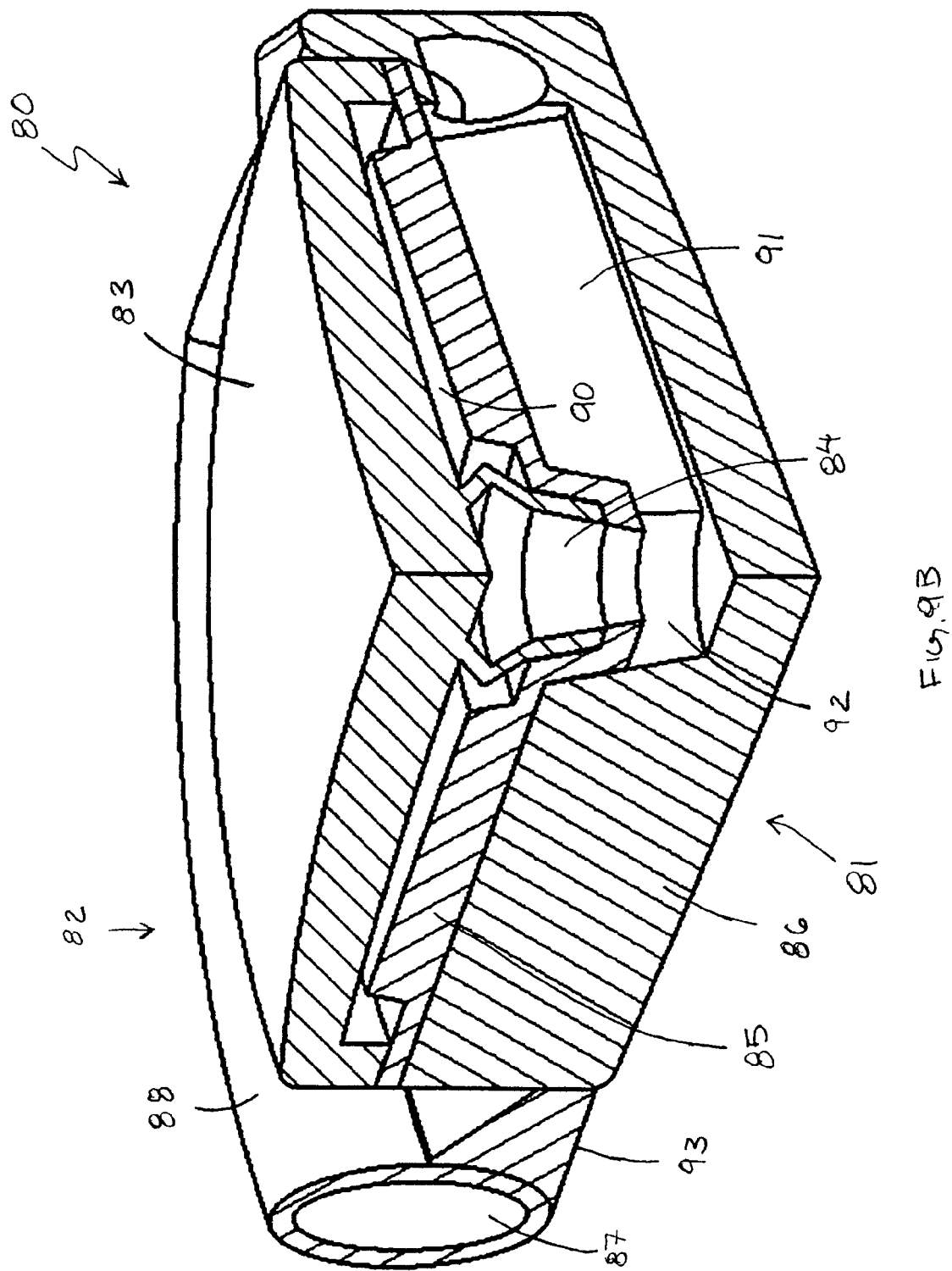

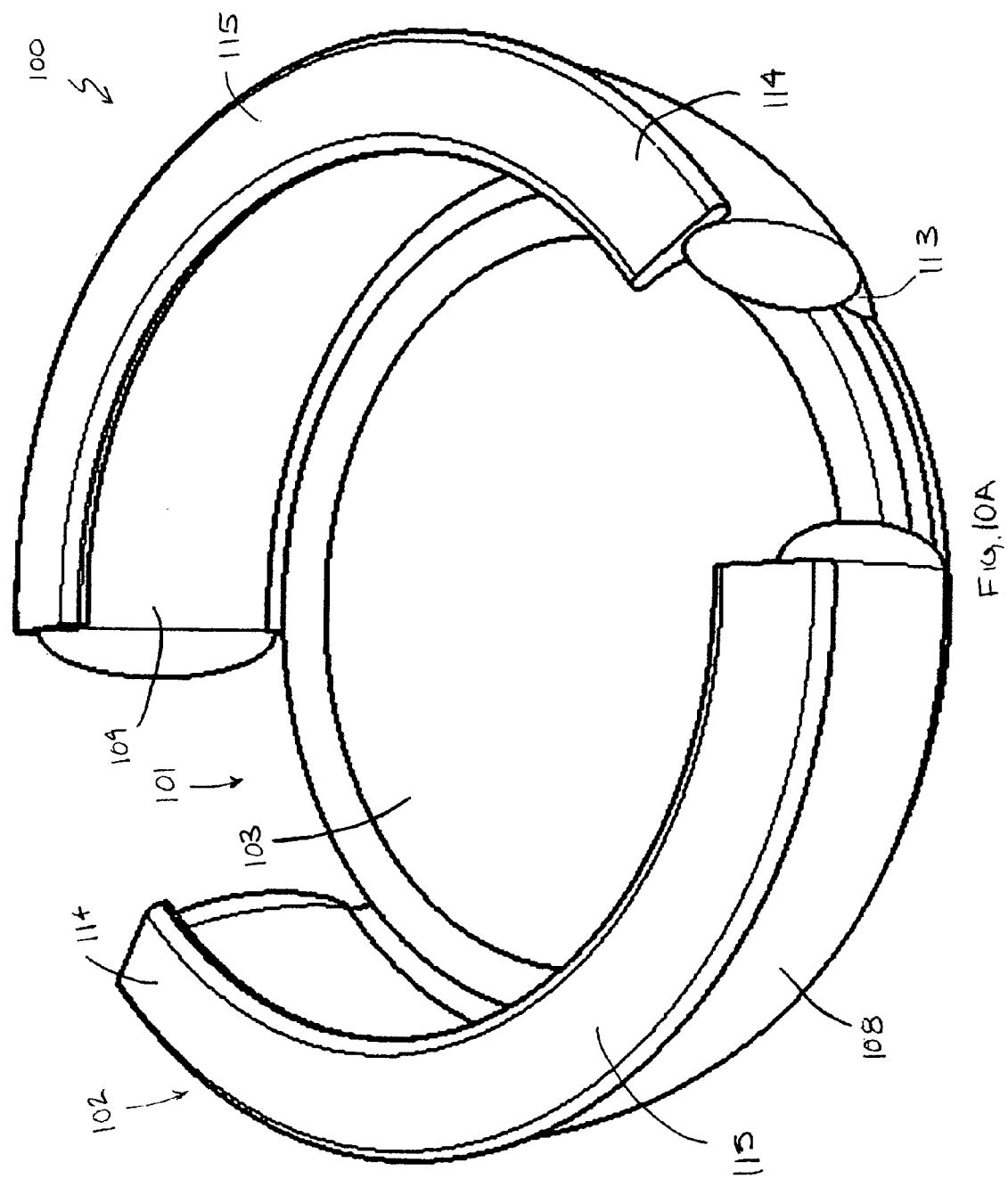

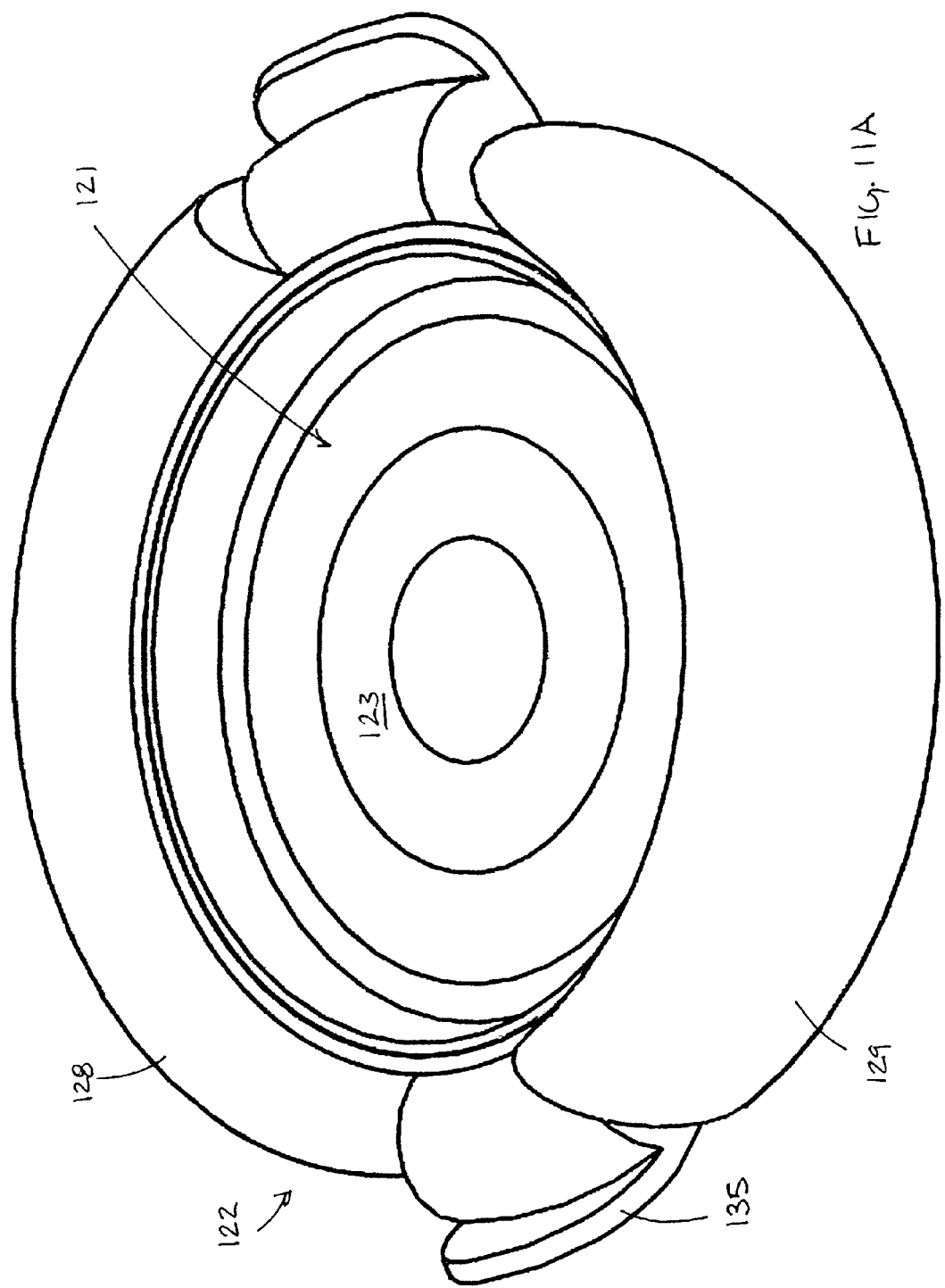

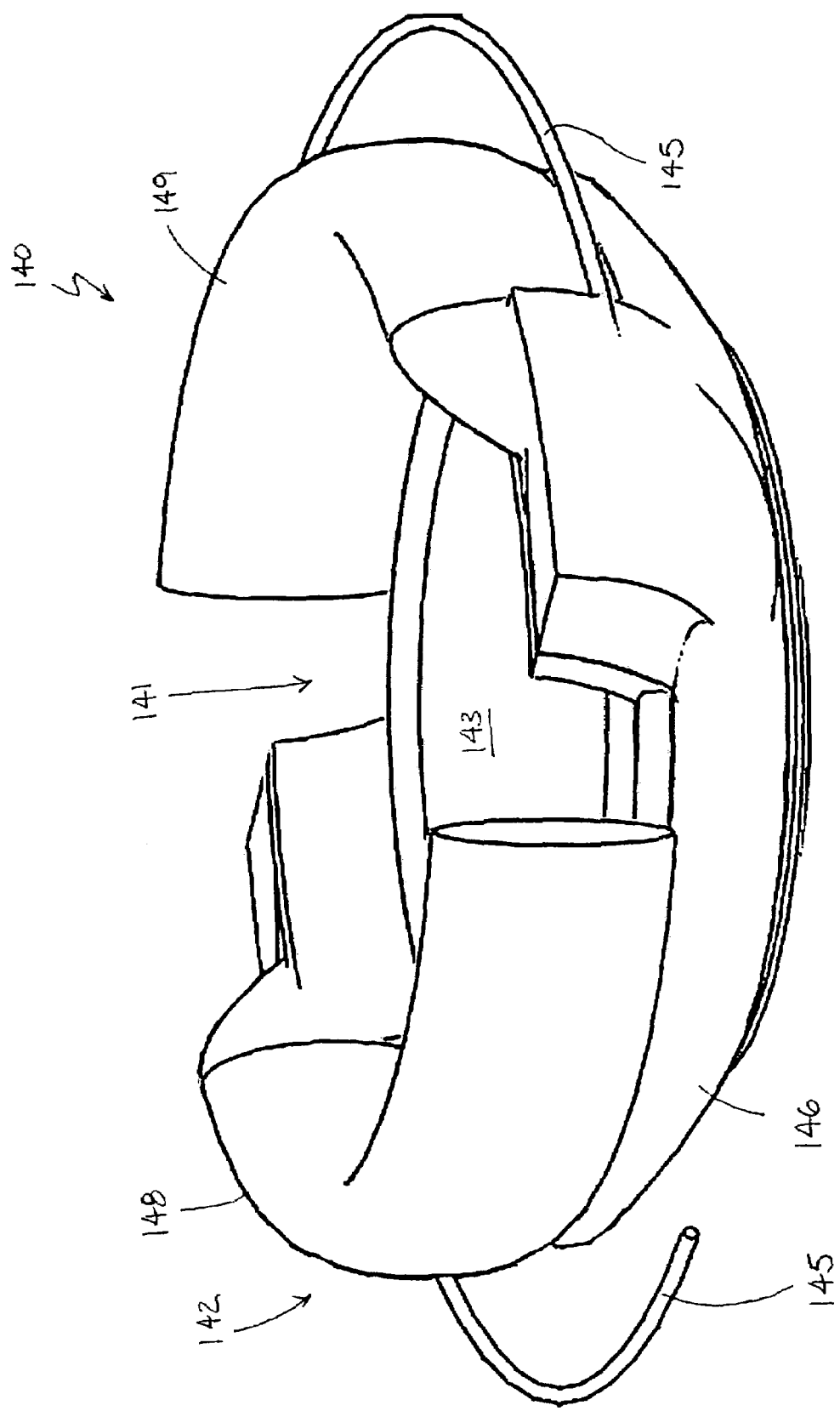

ACCOMMODATING INTRAOCULAR LENS SYSTEM HAVING SPHERICAL ABERRATION COMPENSATION AND METHOD

REFERENCE TO RELATED APPLICATIONS

This application is a continuation-in-part of U.S. application Ser. No. 10/971,598, filed Oct. 22, 2004, now U.S. Pat. No. 7,261,737; which is a continuation-in-part of U.S. application Ser. No. 10/734,514, filed Dec. 12, 2003, now U.S. Pat. No. 7,122,053; and claims the benefit of priority from U.S. provisional application No. 60/433,046, filed Dec. 12, 2002, the disclosures of which are hereby incorporated by reference in their entirety.

FIELD OF THE INVENTION

The present invention relates to intraocular lenses ("IOLs") having optical parameters that are changeable in-situ. More particularly, the invention has application in IOLs for in-capsule implantation for cataract patients or presbyopic patients, wherein movement of the lens capsule applies forces to a circumferentially supported haptic to more efficiently induce transfer of fluid media within the interior of the IOL to alter an optical power of the lens.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule, also referred to herein as "capsular sac," supported by the ciliary muscles via zonules, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein) move between a relaxed state (corresponding to the moderately convex shape) and a contracted state (corresponding to the highly convex shape). Because the lens itself is composed of viscous, gelatinous transparent fibers, arranged in an "onion-like" layered structure, forces applied to the capsule by the ciliary muscles via the zonules cause the lens to change shape.

Isolated from the eye, the relaxed capsule and lens take on a more spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter-muscular mode. Accordingly, when the ciliary muscles are relaxed, the capsule and lens are pulled about the circumference to a larger diameter, thereby flattening the lens, whereas when the ciliary muscles are contracted the lens and capsule relax somewhat and assume a smaller diameter that approaches a more spherical shape.

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition known as "presbyopia". Because the imaging distance is fixed, presbyopia typically entails the need for bi-focals to facilitate near and far vision.

Apart from age-related loss of accommodation ability, such loss is innate to the placement of IOLs for the treatment of cataracts. IOLs are generally single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability.

Although previously known workers in the field of accommodating IOLs have made some progress, the relative complexity of the methods and apparatus developed to date have prevented widespread commercialization of such devices. Previously known devices have proved too complex to be practical to construct or have achieved only limited success, due to the inability to provide accommodation of more than 1-2 diopters.

U.S. Pat. No. 5,443,506 to Garabet describes an accommodating fluid-filled lens wherein electrical potentials generated by contraction of the ciliary muscles cause changes in the index of refraction of fluid carried within a central optic portion. U.S. Pat. No. 4,816,031 to Pfoff discloses an IOL with a hard poly methyl methacrylate (PMMA) lens separated by a single chamber from a flexible thin lens layer that uses microfluid pumps to vary a volume of fluid between the PMMA lens portion and the thin layer portion and provide accommodation. U.S. Pat. No. 4,932,966 to Christie et al. discloses an intraocular lens comprising a thin flexible layer sealed along its periphery to a support layer, wherein forces applied to fluid reservoirs in the haptics vary a volume of fluid between the layers to provide accommodation.

Although fluid-actuated mechanisms such as described in the aforementioned patents have been investigated, currently available accommodating lenses include the Crystalens developed by Eyeonics, Inc. (formerly C&C Vision, Inc.) of Aliso Viejo, Calif. According to Eyeonics, redistribution of the ciliary mass upon constriction causes increased vitreous pressure resulting in forward movement of the lens.

Co-pending, commonly assigned U.S. Patent Application Publication No. 2005/0119740 to Esch et al., which is incorporated by reference herein in its entirety, describes an intraocular lens in which forces applied by the lens capsule to a haptic portion of the lens to induce fluid transfer to and from an actuator disposed in contact with a dynamic surface of the lens.

Another disadvantage of previously known devices is that they oftentimes create spherical aberrations. As is well known in the art, lenses composed of elements having spherical surfaces are easy to manufacture but are not ideal for creating a sharp image because light passing through the elements does not focus on a single focal point. In particular, light that passes through a positive optical element close to the optical axis generally converges at a focal point that is further from the lens than a focal point of light passing through the peripheral portion of the lens, thereby creating under corrected spherical aberration. As a result of spherical aberration in an intraocular lens, all of the light passing through the lens does not focus on the retina resulting in an image that may be blurred and may have softened contrast.

Various devices have been used in optical systems to reduce the effect of spherical aberration. For example, an aperture may be used that limits the ability of light to pass through the peripheral portion of the lens. As a result, the light contributing to the aberration is prevented from passing through the lens. Such a device provides an obvious disadvantage that the amount of light allowed to pass through the lens is reduced. Another way to reduce the effect of spherical aberration is to combine two lenses, one convex and one concave. A still further method of reducing the effects of spherical aberration is to use an aspherical lens. However, such combined lenses and lenses having aspherical profiles are significantly more expensive to produce. In addition, combining lenses requires additional space to house the multiple lenses.

While the lens described in the foregoing Esch application is expected to provide significant benefits over previously-known accommodating lens designs, it would be desirable to provide methods and apparatus for further enhancing conversion of lens capsule movements into hydraulic forces, so as to improve modulation of the lens actuator and dynamic surface.

It also would be desirable to provide methods and apparatus to enhance the efficiency with which loads arising due to natural accommodating muscular action are converted to hydraulic forces.

It also would be desirable to provide methods and apparatus that reduce spherical aberration while maximizing the useful surface area of an accommodating lens design.

SUMMARY OF THE INVENTION

In view of the foregoing, it is an object of the present invention to provide apparatus and methods that restore appropriate optical focusing power action to the human eye.

It is a further object of this invention to provide methods and apparatus wherein a dynamic lens surface may be hydraulically manipulated responsive to movement of the ciliary muscles and lens capsule.

It also is an object of the present invention to provide methods and apparatus for further enhancing conversion of lens capsule movements into hydraulic forces, so as to improve modulation of the lens actuator and dynamic surface.

It is another object of this invention to provide methods and apparatus to enhance the efficiency with which loads arising due to natural accommodating muscular action are converted to hydraulic forces.

It is another object of this invention to provide methods and apparatus for reducing spherical aberration in an accommodating intraocular lens device.

These and other objects of the present invention are accomplished by providing an intraocular lens responsive to forces communicated from the ciliary muscles through the zonules to the capsular bag to operate one or more actuators disposed within the IOL. The actuator is coupled to a dynamic surface of the IOL to deflect the dynamic surface, e.g., from a moderately convex to a highly convex shape, responsive to operation of the one or more actuators. In accordance with the principles of the present invention, the IOL includes at least one secondary deflection mechanism that is configured to further alter the curvature of the dynamic surface to correct for spherical aberration. The secondary deflection mechanism may be alterations of the lens such as varying thickness or inflection points, selection of the boundary condition of the lens, and secondary fluid-mediated actuators.

In an embodiment, the secondary deflection mechanism is a fluid-mediated actuator coupled to a fluid column disposed in at least one haptic of the IOL and a sealed fluid cavity filled with shaping fluid that is adjacent to the dynamic surface. Forces applied to the haptic by the capsular bag, responsive to movement of the ciliary muscles, cause the transfer of fluid between the fluid column and the actuator, which in turn deflects a dynamic surface of the lens.

Deflection of the dynamic surface causes the shaping fluid in the sealed fluid cavity to redistribute which, in turn, alters the shape of the dynamic surface so that it is aspherical. By making the dynamic surface aspherical the total amount of travel required by the actuator may be reduced from approximately 300 microns for non-aspheric lenses to 200 microns. As a result, a more efficient IOL may be produced that requires less influence from the lens capsule.

In a preferred embodiment, the intraocular lens comprises an optic portion including a fluid cavity containing a fixed volume of shaping fluid and a haptic (or non-optic) portion. The optic portion comprises a light transmissive substrate defining one or more fluid channels, at least one actuator coupled in fluid communication with the fluid channels, and anterior and posterior lens elements. At least one of the anterior and posterior lens elements includes a dynamic surface that is operatively coupled to the actuator to cause deflection of the dynamic surface. The other of the anterior or posterior lens elements may be coupled to the substrate or integrally formed therewith.

The haptic portion is disposed at the periphery of the optic portion and comprises one or more haptics that extend outward from the optic portion, each haptic including a fluid channel coupled in fluid communication with a fluid channel in the optic portion. In accordance with one aspect of the present invention, the haptics have a cross-sectional configuration selected so that the internal volume of the haptic is small in an accommodated state. The accommodated state of the haptic is selected to correspond to the accommodated state of the eye, when the ciliary muscles are contracted and anterior/posterior compressive forces applied by the capsular bag to the haptics are reduced.

When the ciliary muscles relax, the zonules pull the capsular sac taut and apply forces to the anterior and posterior faces of the haptic. The forces applied by the capsular sac cause the cross-sectional area of the haptic to increase thereby increasing the internal volume of the haptic. This action in turn causes fluid to be withdrawn from the actuator disposed in the optic portion, so that the dynamic surface of the IOL transitions from an accommodated state to an unaccommodated state. The fixed volume of shaping fluid in the sealed fluid cavity is redistributed in the cavity by movement of the dynamic surface and that redistribution causes the shape of the dynamic surface to be altered.

The actuator used in the optic portion of the IOL may be centrally located within the optic portion that, when filled with fluid, biases the dynamic surface of the IOL to the accommodated state. When the ciliary muscles are contracted, the zonules and capsular bag are less taut, and the haptics are unstressed. Relaxation of the ciliary muscle causes the zonules to transition the capsule to less convex shape, which applies compressive forces to the haptic, thereby withdrawing fluid from the actuator and causing the lens to transition to the unaccommodated state. Alternatively, the actuator may comprise structures disposed at the periphery of the optic portion, so as to further minimize refractive effects and optical aberrations in the optic portion.

Methods of making and using the lens of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIG. 3 is another sectional side view of a human eye illustrating light passing through a spherical lens in the lens capsule;

FIGS. 4A-4C are, respectively, a perspective, exploded perspective and plan view of an exemplary intraocular lens which may be modified to implement the structure and methods of the present invention;

FIG. 5 is a cross-sectional view of a haptic of the intraocular lens of FIGS. 4;

FIG. 6 is a cross-sectional view of the assembled intraocular lens of FIGS. 4;

FIGS. 7A, 7B and 7C are, respectively, cross-sectional views of an intraocular lens optic portion in unaccommodated (FIGS. 7A and 7B), and accommodated configurations (FIG. 7C);

FIGS. 9A and 9B are, respectively, a perspective view and a cross-sectional view of an alternative embodiment of the intraocular lens of the present invention;

FIGS. 10A and 10B are, respectively, a perspective view and a cross-sectional view of an alternative embodiment of the intraocular lens of the present invention;

FIGS. 11A and 11B are, respectively, a perspective view and a cross-sectional view of an alternative embodiment of the intraocular lens of the present invention; and FIG. 12 is a perspective view of an alternative embodiment of the intraocular lens of the present invention.

DETAILED DESCRIPTION OF THE INVENTION

In accordance with the principles of the present invention, an intraocular lens is provided having a haptic portion and a light-transmissive optic portion. The optic portion contains one or more fluid-mediated actuators arranged to apply a deflecting force on a dynamic surface of the lens to provide accommodation. As used herein, the lens is fully "accommodated" when it assumes its most highly convex shape, and fully "unaccommodated" when it assumes its most flattened, least convex state. The lens of the present invention is capable of dynamically assuming any desired degree of accommodation between the fully accommodated state and fully unaccommodated state responsive to movement of the ciliary muscles and lens capsule.

Furthermore, in accordance with the principles of the present invention the optic portion contains one or more secondary deflection mechanism that alters the curvature of the lens. For example, the secondary deflection mechanism may be sealed fluid cavities that are filled with a constant volume of shaping fluid that is redistributed when the lens is actuated between the accommodated and unaccommodated states. As will be discussed in further detail below, when a fluid-mediated actuator applies a deflecting force on a portion of the dynamic surface it causes a portion of a sealed fluid cavity to change in volume. However, because the volume of fluid is fixed, the change in volume in one portion of the cavity causes a complimentary change in volume of another portion, whereby one portion of the dynamic surface becomes more convex at a different rate than another portion. The secondary deflection mechanism also may be integrated into the lens, such as varying thickness or inflection points or areas. As a further alternative, the secondary deflection mechanism may be a boundary condition, i.e., characteristics of the connection of the lens to the remainder of the optic portion around the circumference. As a result of the one or more secondary deflection mechanism, the dynamic surface may be deflected into an aspheric profile, which may be used to correct spherical aberration.

Figure 1:
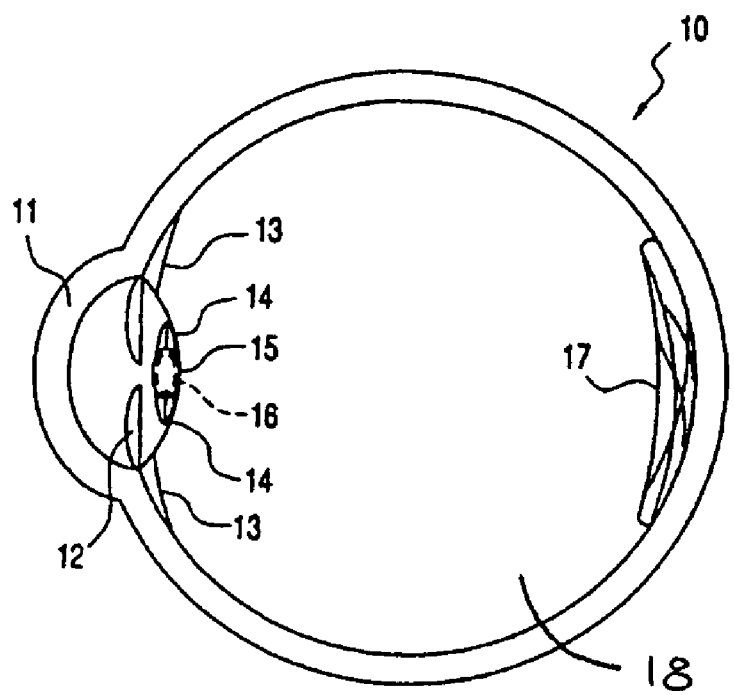
FIG. 1 is a sectional side view of a human eye.

Referring to FIGS. 1 and 2, the structure and operation of a human eye are first described as context for the present invention. Eye 10 includes cornea 11, iris 12, ciliary muscles 13, ligament fibers or zonules 14, capsule 15, lens 16 and retina 17. Natural lens 16 is composed of viscous, gelatinous transparent fibers, arranged in an "onion-like" layered structure, and is disposed in transparent elastic capsule 15. Capsule 15 is joined by zonules 14 around its circumference to ciliary muscles 13, which are in turn attached to the inner surface of eye 10. Vitreous 18 is a highly viscous, transparent fluid that fills the center of eye 10.

Figure 2A:
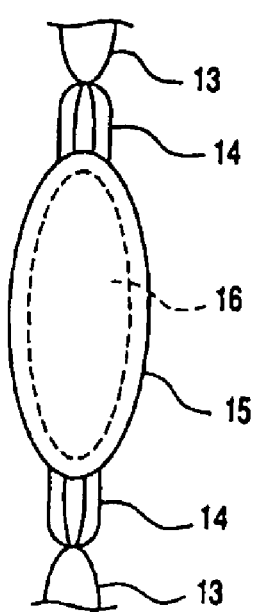
FIGS. 2A and 2B are, respectively, sectional side views of the lens and supporting structures of FIG. 1 illustrating relaxed and contracted states of the ciliary muscles.
Figure 2B:
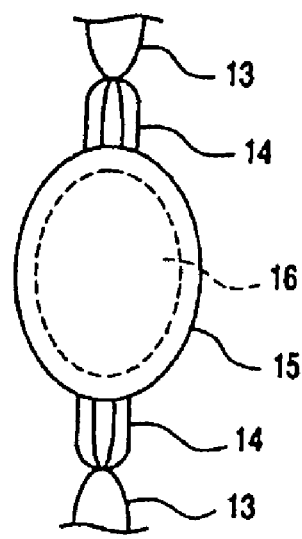

Isolated from the eye, the relaxed capsule and lens take on a convex shape. However, when suspended within the eye by zonules 14, capsule 15 moves between a moderately convex shape (when the ciliary muscles are relaxed) and a highly convex shape (when the ciliary muscles are contracted). As depicted in FIG. 2A, when ciliary muscles 13 relax, capsule 15 and lens 16 are pulled about the circumference, thereby flattening the lens. As depicted in FIG. 2B, when ciliary muscles 13 contract, capsule 15 and lens 16 relax and become thicker. This allows the lens and capsule to assume a more convex shape, thus increasing the diopter power of the lens.

Additionally, various natural mechanisms affect the design requirements of the present invention. For example, during accommodation the pupil naturally stops down (i.e., reduces in diameter) which reduces the area of the natural lens that transmits light. In addition, the eye will experience the Stiles-Crawford Effect which also reduces the effective area of the natural lens. In particular, the brightness of light rays incident on cones in the eye is dependent on the angle at which those rays are incident on the cones. In particular, light rays that strike the cones perpendicular to their surface appear brighter than those that do not. As a result, the light rays passing through the periphery of the lens are less significant for proper vision.

Accommodating lenses that are currently commercially available, such as the Crystalens device developed by Eyeonics, Inc., Aliso Viejo, Calif., typically involve converting movements of the ciliary muscle into anterior and posterior translation of an optic portion of the IOL relative to the retina. Such devices do not employ the natural accommodation mechanisms described above with respect to FIGS. 1-2, but instead rely directly on changes in vitreous pressure to translate the lens.

Referring now to FIG. 3, a simplified schematic is provided of the spherical aberration effects of implanting spherical lens 19 within capsule 15 thereby introducing spherical aberrations. In particular, light rays L passing through a central portion of spherical lens 19, i.e., near the optical axis, converge at location A on retina 17. However, light rays L passing through the peripheral portion of spherical lens 19 converge at location B which is spaced from location A and retina 17. Because location B is spaced from retina 17, when those light rays reach retina 17 they are dispersed. Although only two focal points are illustrated in FIG. 3, it should be appreciated that light rays passing through lens 19 will focus at many different focal points along the optical axis of the lens and the distance of any particular focal point from retina 17 depends on the radial location on lens through which the light rays pass.

Referring now to FIGS. 4-6, an exemplary embodiment of an intraocular lens suitable for implementing the structure of the present invention is described, such as is described in the commonly assigned U.S. Patent Application No. 2005/0119740 to Esch et al., which is incorporated herein by reference. For completeness of disclosure, details of the IOL described in that application are provided below.

IOL 20 comprises optic portion 21 and haptic portion 22. Optic portion 21 is constructed of light transmissive materials, while haptic portion 22 is disposed at the periphery of the optic portion and does not participate in focusing light on the retina of the eye.

Optic portion 21 comprises anterior lens element 23 including actuator 24 (see FIG. 6), intermediate layer 25 and posterior lens element 27, also referred to herein as "substrate," all made of light-transmissive materials, such as silicone or acrylic polymers or other biocompatible materials as are known in the art of intraocular lenses. Illustratively, actuator 24 comprises a bellows structure that is integrally formed with anterior lens element 23. It will be appreciated that actuator 24 may alternatively be integrally formed with intermediate layer 25, if desired. Optic portion 21 is illustratively described as comprising three layers, although it will be apparent that other arrangements may be employed.

Anterior lens element 23, actuator 24 and intermediate layer 25 are spaced from each other and lens element 23 and intermediate layer 25 are sealably coupled at their circumferences to define cavity 34 therebetween. Cavity 34 is filled with a fixed volume of shaping fluid. The shaping fluid is light-transmissive fluid, preferably silicone or acrylic oil or another suitable biocompatible fluid, and is selected to have a refractive index that matches the materials of anterior lens element 23, actuator 24, intermediate layer 25 and posterior lens element 27. Furthermore, the viscosity of shaping fluid is selected so that shaping fluid may be easily distributed within cavity 34 in response to relative motion between anterior lens element 23, actuator 24 and intermediate layer 25.

Haptic portion 22 illustratively comprises haptics 28 and 29 that extend from substrate 26. Each of haptics 28 and 29 includes an interior volume 30 that communicates with channel 31 in substrate 26. Actuator 24 is disposed in well 32 formed in intermediate layer 25 and substrate 27, so that a lower end of the actuator seats within well 32. Haptics 28 and 29 may include resilient support members 33 (see FIGS. 5 and 6) that urge haptics 28, 29 radially outward to ensure that haptics 28, 29 seat against the capsular equator and ensure that optic portion 21 remains centered in capsule 15. It should be appreciated that support members 33 need not form a portion of the structure of haptics 28, 29, but instead may be separate components that primarily ensure that optic portion 21 remains centered, as will be described in further detail with reference to additional embodiments below.

Although channel 31 and well 32 are depicted in FIG. 6 having their side walls disposed parallel to the optical axis of the lens, it is expected that all such surfaces may be arranged obliquely relative to the optical axis of IOL 20. Such an arrangement is expected to reduce the potential to create spurious reflections in light passing along the optical axis of the IOL. It should be understood that such arrangements may be beneficially employed throughout the IOLs described in this specification.

As depicted in FIG. 5, each of haptics 28, 29 has an undeformed state and may be transitioned to a deformed state (shown in dotted line in FIG. 5) by application of compressive forces (shown by arrows C) to the anterior and posterior surfaces of haptic 28, 29. Haptics 28 and 29 are configured so that the interior volumes of the haptics increase as the haptics deform from the undeformed, unstressed state to the deformed state. The undeformed, unstressed state depicted by the solid lines in FIG. 5 corresponds to a fully-contracted state of the ciliary muscles, as described herein below.

Actuator 24 is disposed in well 31 of intermediate layer 25 and substrate 27, and preferably comprises a sturdy elastomeric material. Intermediate layer 25 and actuator isolate fluid in channel 31, well 32 and the interior of actuator 24 from the shaping fluid disposed in cavity 34. The fluid disposed within channel 31, well 32 and actuator 24, preferably comprises silicone or acrylic oil or another suitable biocompatible fluid, and is selected to have a refractive index that matches the materials of anterior lens element 23, actuator 24, intermediate layer 25 and posterior lens element 27.

Illustratively, actuator 24 comprises a bellows structure integrally formed with anterior lens element 23, and is configured to deflect anterior lens element 23 responsive to fluid pressure applied within the bellows by haptics 28, 29. Alternatively, actuator 24 may be fabricated as a separate component and glued or otherwise bonded to anterior lens element 23 and intermediate layer 25.

Deflection of the anterior lens element resulting from movement of actuator 24 causes the anterior lens element to transition between an accommodated state, in which the lens surface is more convex, to an unaccommodated state, in which the lens surface is less convex. As will of course be understood, optic portion could instead be arranged so that actuator 24 deflects posterior lens element 27. Still further, the actuator may be configured to induce a major deflection of one lens element and a minor deflection of the other lens element; the arrangement depicted in FIGS. 4 is intended to be illustrative only.

The inner surface and thickness of anterior element 23 (relative to the optical axis of the lens) are selected so that the outer surface of anterior lens element 23 retains an optically corrective shape throughout the entire range of motion of actuator 24, e.g., for accommodations 0-10 diopters. It should of course be understood that the inner surface and thickness of anterior element 23 may be selected to provide an aspherical outer surface in combination with the deforming characteristics of the shaping fluid within cavity 34 of the present invention, as required for a desired degree of optical correction.

While IOL 20 includes a single actuator 24 located at the center of optic portion 21, the IOL alternatively may include an array of actuators spaced apart in any predetermined configuration on the posterior surface of the anterior lens element, as may be required to impose a desired pattern of localized deflection on the anterior lens element. As will be apparent to one of skill in the art, an annular structure may be substituted for the individual actuator depicted in FIG. 5, and the side walls of the actuator may be of any suitable shape other than a bellows structure. For example, the actuator may comprise a polymer that had been treated, such as by application of bi-axial stress, to pre-orient the polymer to stretch predominantly in a desired direction.

IOL 20 also may include coating 35 disposed on all interior fluid-contacting surfaces within IOL 20, such as fluid channel 31 and well 32 and the surfaces defining cavity 34. Coating 35 is configured to reduce or prevent diffusion of the index-matched fluid used to drive actuator 24, and within cavity 34, from diffusing into the polymer matrix of the lens components and/or to prevent inward diffusion of external fluids into the IOL. The IOL also may include coating 36, which comprises the same or a different material than coating 35, disposed on the exterior surfaces of the lens. Coating 36 is intended to serve as a barrier to prevent the diffusion of fluids from the eye into the IOL or from the IOL into the eye, and may be disposed on the entire exterior surface of the optic portion and haptic portion, including the anterior and posterior lens elements and haptics.

Alternatively, both coatings 35 and 36 may be layered onto a single surface to prevent or reduce both ingress of bodily fluids into the IOL or fluid circuit, and loss of index-matched fluid from the interior spaces of the IOL. Coatings 35 and 36 preferably comprise a suitable biocompatible polymer, perfluorinated hydrocarbon, such as PTFE, inorganic (e.g., silicone dioxide) or metallic layer (e.g., nickel-titanium) applied by any of a variety of methods known in the art.

Operation of IOL 20 of FIGS. 4-6 is now described. IOL 20 is implanted within a patient's capsule after extraction of the native lens using any suitable technique. When implanted, haptics 28 and 29 support the IOL so that optic portion 21 is centered along the central axis of eye. When the ciliary muscles are in a contracted state, the zonules and capsule are less taut, and the haptics 28 and 29 are in the undeformed state. In this condition, fluid pressure applied by the fluid in the haptics, channel 31 and well 32 maintain actuator 24 fully extended, so that anterior lens element 23 is deflected to its accommodated state.

When the ciliary muscles relax, the zonules pull the capsule taut, thereby applying compressive forces on the anterior and posterior surfaces of haptics 28, 29. These forces cause haptics 28, 29 to deform to the deformed state depicted by the dotted lines in FIG. 5, thereby increasing interior volume 30 of haptics 29, 30. Because there is only a predetermined amount of fluid contained within the interior of haptics 28, 29, channel 31, well 32 and actuator 24, the increased interior volume 30 in deformed haptics 28, 29 draws fluid from within actuator 24. This in turn causes actuator 24 to shorten, thereby deflecting anterior lens element 23 to a less convex, unaccommodated state. Subsequent contraction and relaxation of the ciliary muscles causes the foregoing process to repeat, thereby providing a degree of lens accommodation that mimics the accommodating action of the natural lens.

As described above, spherical lenses may introduce spherical aberrations. The inner surface and thickness of anterior element 23 may be selected to provide an aspherical outer surface to lessen the spherical aberration through the lens. The present invention is directed to an IOL having another structural feature that alters the shape of the dynamic lens surface to further lessen the effects of spherical aberrations.

Figure 7A:
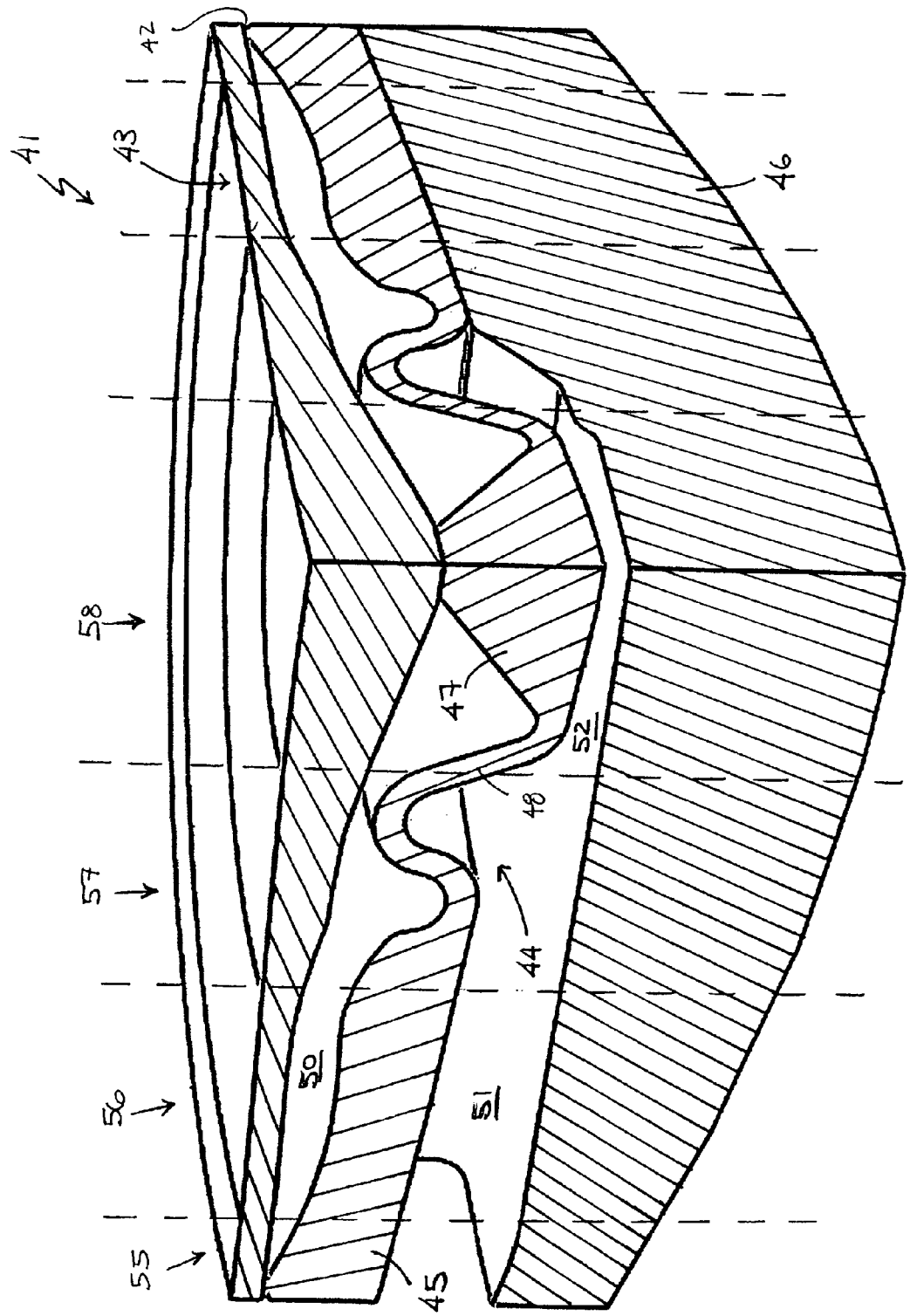
Figure 7B:
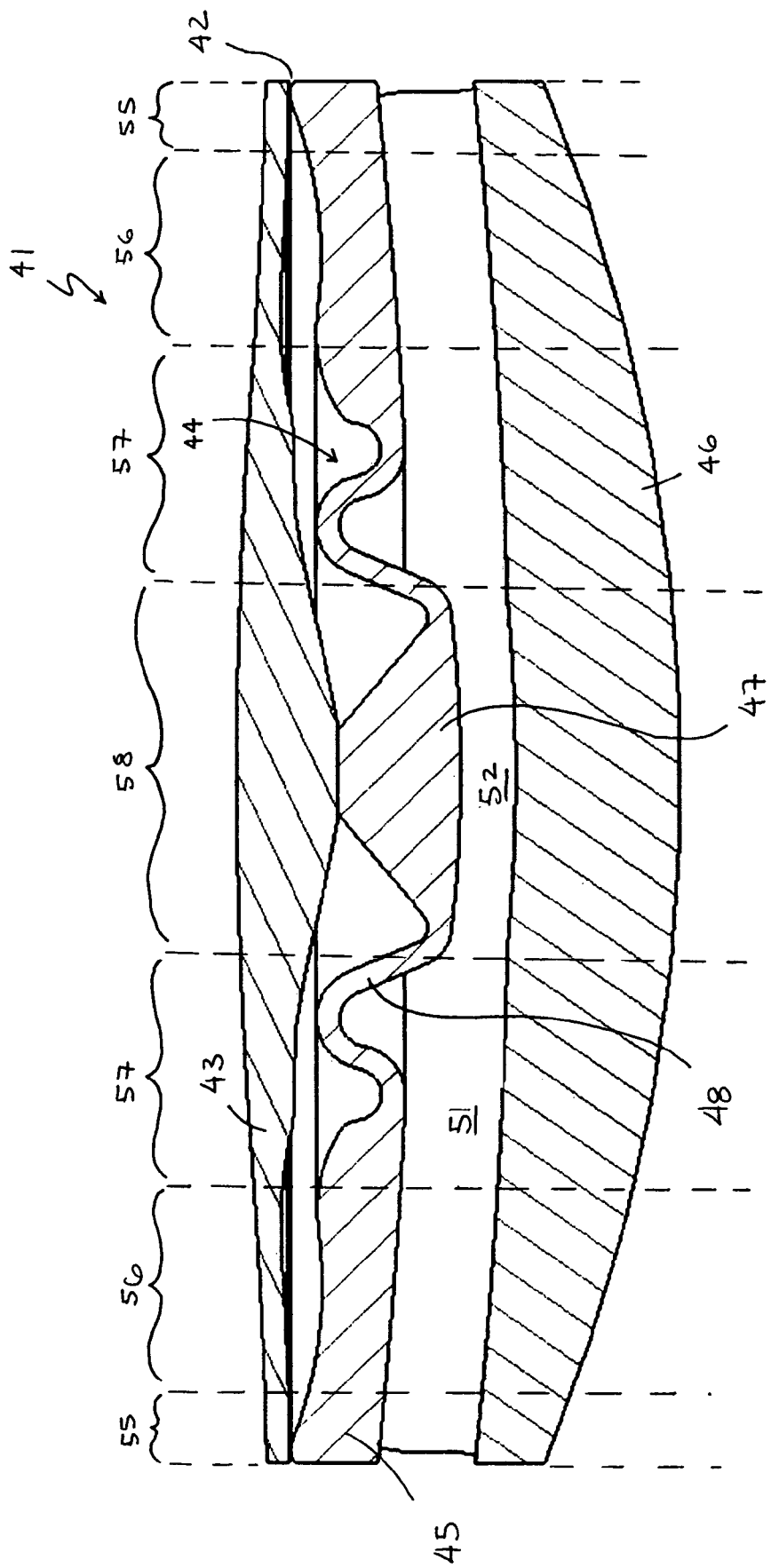

Referring to FIGS. 7A, 7B and 7C, an embodiment of optic portion 41 of an IOL constructed in accordance with the principles of the present invention is described. Optic portion 41 includes anterior lens element 43, intermediate layer 45, actuator 44 and substrate 46. In the present embodiment, intermediate layer 45 is integral with actuator 44. Similar to the above-described embodiment, the components of optic portion 41 are made of light-transmissive materials, such as silicone or acrylic polymers or other biocompatible materials as are known in the art of intraocular lenses.

Actuator 44 includes projection 47 and flexible wall 48 that circumscribes projection 47. Wall 48 forms a generally annular undulation, or corrugation, and extends between a substantially stationary portion of intermediate layer 45 and projection 47. Similar to the above-described embodiment, actuator 44 is in fluid communication with deformable haptics (not shown) that are used to distribute a fluid between the haptics, channel 51 in substrate 46 and well 52 that is located adjacent actuator 44.

Deformation of the haptics by action of the ciliary muscles causes the interior volume of the haptics to change, which may either force fluid through channel 51 toward well 52 or draw fluid through channel 51 from well 52. Forcing fluid into well 52 causes the fluid pressure within well 52 to increase, which increases the force placed on actuator 44. An increase in pressure in well 52 causes projection 47 to translate in an anterior direction. Conversely, when fluid is drawn from well 52, pressure within well 52 decreases and projection 47 translates in a posterior direction. In the present embodiment, translation of projection 47 is permitted by flexing of the wall of actuator 44 adjacent projection 47. Projection 47 is coupled to anterior lens element 43 so that movement of projection 47 causes anterior lens element 43 to deform.

Anterior lens element 43 and intermediate layer 45 are coupled to each other at their circumferences to provide a fluid seal 42 between the two components. As a result of fluid seal 42, fluid cavity 50 is formed between anterior lens element 43 and intermediate layer 45. Anterior lens element 43 and intermediate layer 45 may be coupled by adhering, welding or any other technique recognized in the art for creating a fluid seal. For example, in an embodiment, an index-matched adhesive, such as an acrylic monomer, couples anterior lens element 43 and intermediate layer 45. However, it will be appreciated that any biocompatible adhesive may be employed.

Fluid cavity 50 is filled with a substantially fixed volume of shaping fluid. Coatings may be applied to the surfaces of cavity 50 to reduce or prevent diffusion of the shaping fluid from cavity 50.

For the purpose of further discussion, optic portion 41 will be described with reference to boundary zone 55, outer peripheral zone 56, inner peripheral zone 57 and central zone 58. Boundary zone 55 is located the furthest radially outward from the optical axis of optic portion 41 and includes the sealed coupling between anterior lens element 43 and intermediate layer 45. Boundary zone 55 includes a portion of cavity 50 located the furthest radially outward from the optical axis and fluid seal 42.

Outer peripheral zone 56 is located adjacent and radially inward from boundary zone 55. Outer peripheral zone 56 of optic portion 41 includes a large portion of intermediate layer 45 and cavity 50. In the present embodiment, anterior lens element 43 has a reduced thickness and is flexible in outer peripheral zone 56. In addition, the anterior surface of intermediate layer 45 may be generally concave so that it curves away from anterior lens element 43, thereby forming an enlarged region of cavity 50 and an enlarged space between anterior lens element 43 and intermediate layer 45.

Inner peripheral zone 57 is located adjacent and radially inward from outer peripheral zone 56. Inner peripheral zone 57 includes a portion of cavity 50 that is located between anterior lens element 43 and wall 48 of actuator 44.

Central zone 58 is located further radially inward from inner peripheral zone 57. The optical axis of optic portion 41 extends through central zone 58 and central portion of anterior lens element 43 and projection 47 are disposed within central zone 58.

As described above, deformation of the haptics by action of the ciliary muscles and capsule causes the interior volume of the haptics to change, thereby causing actuator 44 and anterior lens element 43 to move. The portions of cavity 50 within each of boundary zone 55, outer peripheral zone 56, inner peripheral zone 57 and central zone 58 each have a first volume when optic portion 41 is in the unaccommodated state shown in FIGS. 7A and 7B. When movement of actuator 44 and translation of projection 47 causes optic portion 41 to transition to the accommodated state, shown in FIG. 7C, there is a resultant change in the shape of cavity 50 and each of the portions of cavity 50 experiences a change to a second volume.

During the transition of optic portion 41 from the unaccommodated state to the accommodated state, the total volume of cavity 50 remains constant, but the volume of portions of cavity 50 may change. In particular, the volumes of the inner peripheral and central portions of cavity 50 generally increase as projection 47 translates and forces anterior lens element 43 anteriorly. The increase in volume of those portions causes the shaping fluid contained within cavity 50 to be drawn into that increased volume from the outer peripheral and boundary portions of cavity 50. As the shaping fluid is drawn from those outer portions, it reduces pressure in those outer portions of cavity 50, thus causing the outer portions of anterior lens element 43 to be drawn toward intermediate layer 45, as shown in FIG. 7C, thereby reducing the volume of those portions.

The shape of cavity 50 and resulting changes in volume of the various portions of cavity 50 result in the central and inner peripheral portions of anterior lens element 43 being generally more convex than the boundary and outer peripheral portions of cavity 50. It will be appreciated that the boundary and outer peripheral portions of anterior lens element 43 may be convex, concave or flat as desired because due to the stopping down of the pupil and/or the Stiles-Crawford Effect light passing through those portions may be less significant for proper vision.

It should be appreciated that the shape of cavity 50 may be selected by creating intermediate layer 45 and anterior lens element in any desired shape and thickness. The shapes and thicknesses of those components may be used to create any desired changes in the volumes of the various portions of the cavity 50 and to create any desired pressure changes during movement of actuator 44. Furthermore, the change in volume of the various portions of cavity 50 may be controlled by adjusting the elasticity of each of the corresponding portions of anterior lens element 43, intermediate layer 45 and actuator 44.

It should also be appreciated that the boundary condition, i.e., the configuration of the interface of intermediate layer 45 and anterior lens element 43 may be selected to create relative motion between those components in boundary zone 55. For example, as shown in the present embodiment, anterior lens element 43 and intermediate layer 45 may be rigidly fixed so that there is no relative movement between the components at the location of fluid seal 42 between the parts. Alternatively, the sealed coupling between anterior lens element 43 and intermediate layer 45 may be configured to allow limited relative motion between the parts. For example, fluid seal 42 may include a bellows or hinge member that allows relative motion.

Figure 8A:
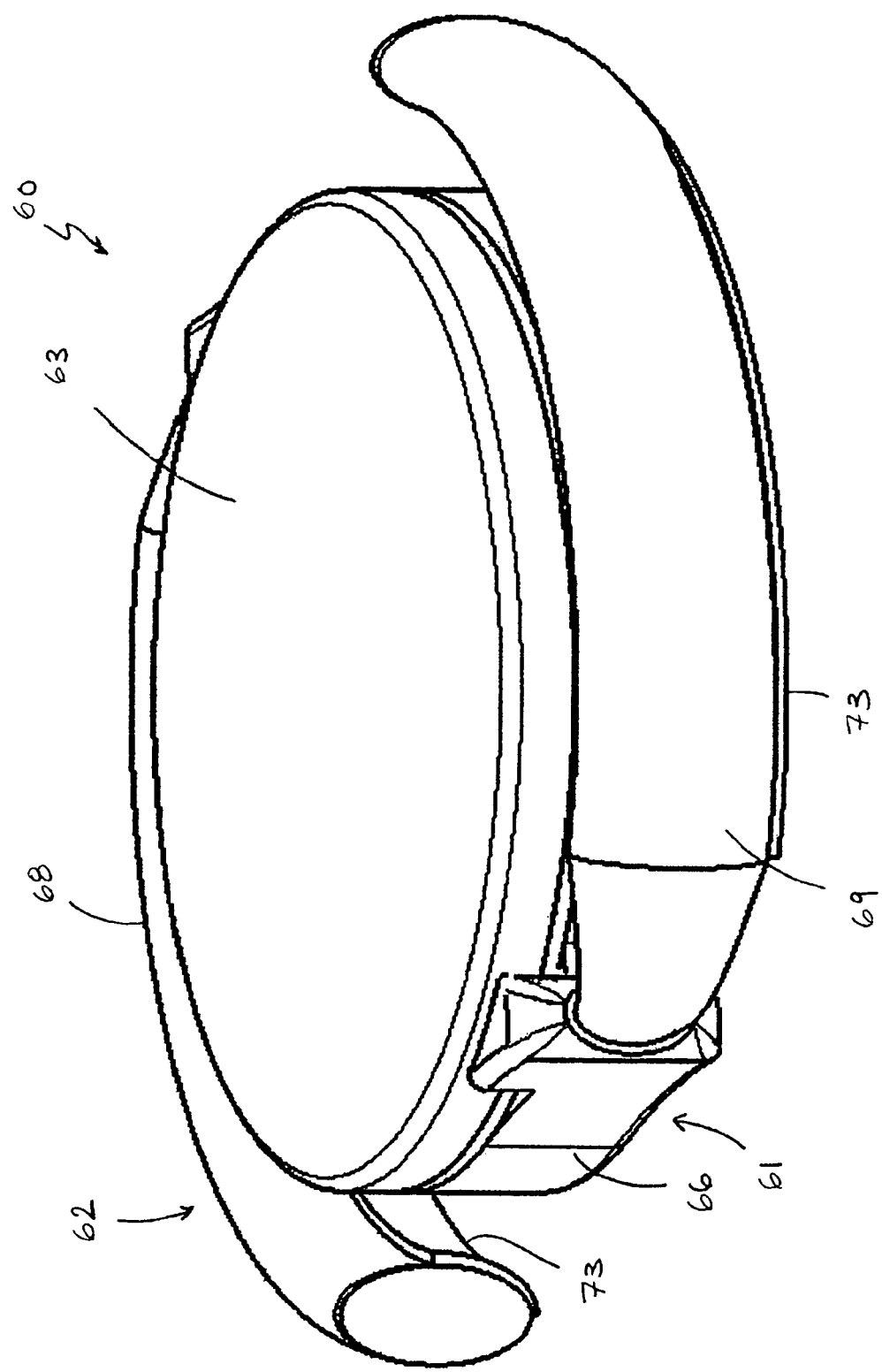
FIGS. 8A and 8B are, respectively, a perspective view and a cross-sectional view of an illustrative embodiment of the intraocular lens of the present invention.
Figure 8B:
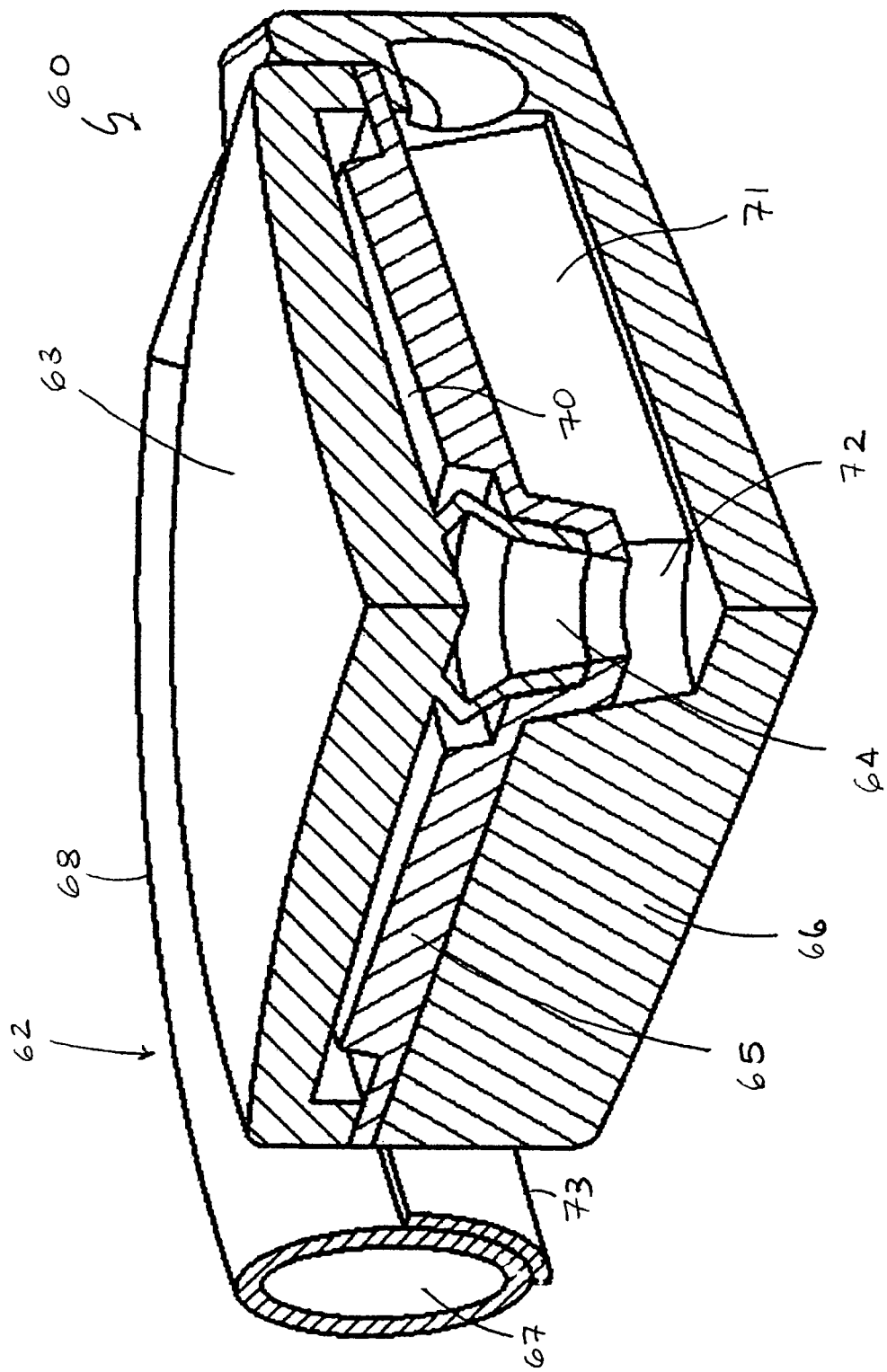

Referring now to FIGS. 8A and 8B, an embodiment of an IOL constructed in accordance with the principles of the present invention is described. IOL 60 utilizes a sealed cavity 70 and shaping fluid to create an aspherical accommodated lens. Additionally, IOL 60 includes backstops 73 for maximizing the hydraulic forces generated by asymmetric loads imposed during transition of the lens capsule between the accommodated and unaccommodated states. IOL 60 generally includes optic portion 61 and haptic portion 62, both of which are similar in construction to the corresponding portions of the embodiment of FIGS. 4-6. In particular, optic portion 61 includes anterior lens element 63, actuator 64, intermediate layer 65 and substrate 66.

Haptic portion 62 includes haptics 68, 69, each of which defines interior volume 67 that is in fluid communication with channel 71 and well 72 formed in substrate 66. Because the structure of the components is substantially identical to the corresponding structures of IOL 20 described above, these components will not be described in further detail.

In accordance with the principles of the present invention, IOL 60 further comprises cavity 70 which is a fluidly sealed cavity defined by anterior lens element 63 and intermediate layer 65. Cavity 70 contains a substantially fixed volume of shaping fluid. Which is distributed through cavity 70 when actuator 64 forces anterior lens element 63 to move under the influence of haptic portion 62.

In the present embodiment, intermediate layer 65 is a separate component from actuator 64 and as a result, a fluid seal is provided both between anterior lens element 63 and intermediate layer at the periphery of optic portion 61 as well as between intermediate layer 65 and actuator 64 near the center of optic portion 61.

IOL 60 further comprises backstops 73 that rigidly support at least a portion of the circumference of each of haptics 68 and 69. Backstops 73 are coupled to a portion of the outer surface of each haptic 68, 69 and are cantilevered members that generally follow the substantially toroidal shape of haptics 68, 69.

The present embodiment combines the shaping fluid included in cavity 70 and backstops 73 to more efficiently convert movement of a lens capsule into hydraulic forces in IOL 60 and to prevent or reduce resulting spherical aberration.

Referring now to FIGS. 9A and 9B, an alternative embodiment of an IOL constructed in accordance with the principles of the present invention is described. IOL 80 generally includes optic portion 81 and haptic portion 82, both of which are similar in construction to the corresponding portions of the embodiments described above. In particular, optic portion 81 includes anterior lens element 83, actuator 84, intermediate layer 85 and substrate 86.

Haptic portion 82 includes haptics 88 and 89, each of which define interior volume 87 that is in fluid communication with channels 91 and well 92 that are formed in substrate 86. Because the structure of the components is substantially identical to the corresponding structures of the previously described embodiment these components will not be described in further detail.

IOL 80 also includes sealed cavity 90 that contains shaping fluid. As described above, movement of actuator 84 and anterior lens element 83 causes changes in the volumes of portions of cavity 90 which in turn causes the shaping fluid to be redistributed within cavity 90. The redistribution of the shaping fluid causes changes in pressure within cavity 90 which causes further deflection of anterior lens element 83 generally to an aspheric shape.

Backstops 93 also are provided in IOL 80, and extend from optic portion 81 to haptics 88 and 89. Backstops 93 are generally shaped as sections of a disk or cone. Similar to the backstops described with regard to the previous embodiment, backstops 93 provide support to a portion of haptics 88, 89 so that movement of the lens capsule is more efficiently converted into deformation of haptics 88, 89 rather than into translation of haptics 88, 89.

Figure 10B:
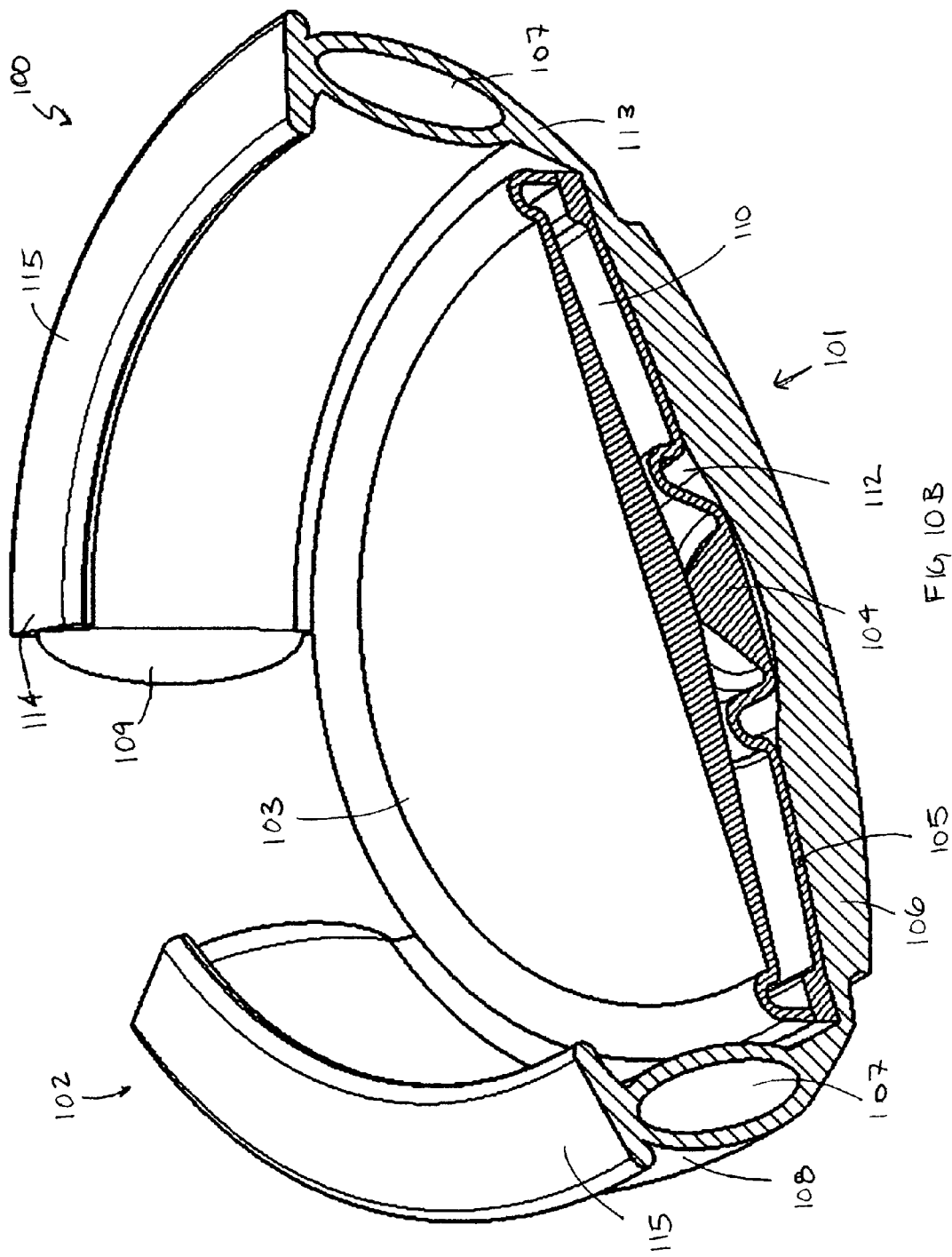

Referring to FIGS. 10A and 10B, an additional embodiment of an IOL constructed in accordance with the principles of the present invention is described. Similar to the previously described embodiments, IOL 100 generally includes optic portion 101 and haptic portion 102. Optic portion 101 includes anterior lens element 103, substrate 106 and actuator 104 interposed therebetween. In the present embodiment, actuator 104 also forms an intermediate layer and substrate 106 may function as a posterior lens element.

In accordance with the present invention, IOL 100 includes a sealed cavity 110 that is formed between intermediate layer 105, actuator 104 and anterior lens element 103. Cavity 110 is filled with a substantially constant volume of shaping fluid that is redistributed through cavity 110 when actuator 104 moves anterior lens element. Cavity 110 is fluidly sealed by a seal between anterior lens element 103 and intermediate layer 105 formed by the circumferential coupling of those components.

Haptic portion 102 includes haptics 108 and 109, each of which defines interior volume 100 that is in fluid communication with channels (not shown) and well 101 that are formed between actuator 104 and substrate 106. Each haptic 108, 109 is integrated into substrate 106 and extends backstop portion 113 of substrate 106. Backstop 113 is configured to provide support over a posterior portion of haptics 108, 109. It should be appreciated that the dimensions of haptics 108 and 109 and backstop portion 113 are selected so that backstop portion 113 is significantly more rigid than haptics 108, 109 so that haptics are permitted to deform when acted upon by the lens capsule.

Additionally, load shelf 114 is provided on an anterior portion of each haptic 108, 109 that is approximately diametrically opposed to backstop 113. Shelf 104 includes anterior surface 115 that is configured to engage a portion of the anterior wall of a lens capsule. Anterior surface 115 provides a greater surface area upon which force may be exerted on haptic 108, 109 by the lens capsule. As a result, energy from movement of the capsular bag may be captured more efficiently and converted into deformation of haptic 109, 98 and hydraulic forces within IOL 100.

The present embodiment also illustrates an alternative boundary condition between anterior lens element 103 and intermediate layer 105. In particular, anterior lens element 103 includes an undulation similar to that of actuator 104 and a wall section of anterior lens element 103 that is oriented in the anterior/posterior direction is coupled to intermediate layer 105. As a result of that wall section, the peripheral portion of anterior lens element 103 may be permitted to bend more freely when actuator 104 deforms anterior lens element 103 and redistributes the shaping fluid within cavity 110.

Figure 11B:
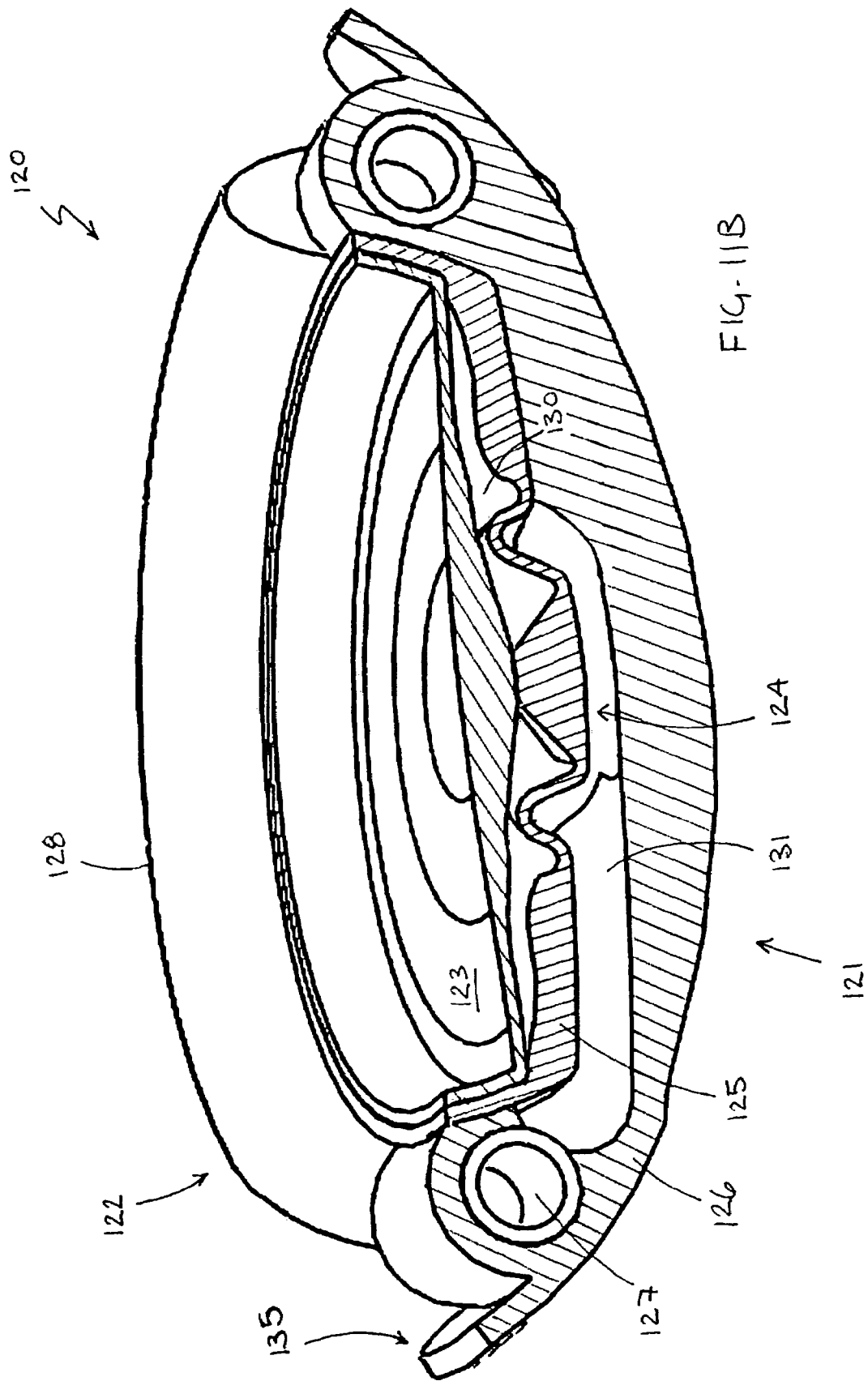

Referring now to FIGS. 11A and 11B, an embodiment of an IOL constructed in accordance with the principles of the present invention is described. IOL 120 utilizes sealed cavity 130 and shaping fluid to create an aspherical accommodated lens while maximizing the hydraulic forces generated by asymmetric loads imposed during transition of the lens capsule between the accommodated and unaccommodated configurations. IOL 120 generally includes optic portion 121 and haptic portion 122, both of which are similar in construction to the corresponding portions of the embodiments described above. In particular, optic portion 121 includes anterior lens element 123, actuator 124, intermediate layer 125 and substrate 126.

Haptic portion 122 includes haptics 128, 129, each of which define interior volume 127 that is in fluid communication with channels 131 and well 132 that are formed in substrate 126. Because the structure of the components is substantially identical to the corresponding structures of the embodiments described above, these components will not be described in further detail.

IOL 120 also includes capsule support members 135 that are located external of haptics 128, 129. Support members 135 are tab-shaped features that extend radially outward and are configured to engage the inner wall of a lens capsule so that the capsule is held in a more taut configuration so that engagement between haptics 128, 129 and the lens capsule is maintained when the ciliary muscles are relaxed or contracted. Maintaining that engagement more efficiently converts movement of the lens capsule to deformation of haptics 128, 129. Support members 135 are preferably located adjacent to the coupling of haptics 128, 129 to optic portion 121, because deformation of that portion of haptics 128, 129 is not relied upon for moving fluid in IOL 120. It should be appreciated however that support members 135 may be located anywhere that will not prevent haptics 128, 129 from deforming sufficiently to transition optic portion 121 between the accommodated and unaccommodated configurations.

Referring now to FIG. 12, an embodiment of an IOL constructed in accordance with the principles of the present invention is described. IOL 140 utilizes a sealed cavity and shaping fluid to create an aspherical accommodated lens while maximizing the hydraulic forces generated by asymmetric loads imposed during transition of the lens capsule between the accommodated and unaccommodated configurations. IOL 140 generally includes optic portion 141 and haptic portion 142, both of which are similar in construction to the corresponding portions of the previously described embodiments.

The present embodiment illustrates an alternative construction of support members 145. Support members 145 are generally wires that circumscribe haptic portion 142 radially outward from each of haptics 148, 149. Each support member 145 is preferably coupled to haptic portion 142 where each of haptics 148, 149 is coupled to optic portion 141.

Support members 145 are configured to engage the inner wall of a lens capsule so that the capsule is held in a more taut configuration so that engagement between haptics 148, 149 and the lens capsule is maintained when the ciliary muscles are relaxed or contracted. Maintaining that engagement more efficiently converts movement of the lens capsule to deformation of haptics 148, 149.

In addition to utilizing the sealed cavities containing a fixed volume of shaping fluid, the flexibilities and shapes of the components may be selected to tailor the influence of the shaping fluid. In particular, the thickness and material of the anterior lens component may be selected to provide an desired deflection. In addition, the shape of the sealed cavity may be selected by altering the shapes of the adjacent components to provide any desired change in volume for any portion of the cavity.

It should be appreciated that although each embodiment has been described having one sealed cavity, any number of sealed cavities containing shaping fluid may be included. For example, sealed cavities may be included adjacent to any desired portion of the lens element so that discrete portions of the lens element may be shaped in a desired fashion.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An intraocular lens configured for implantation in a capsular sac following extraction of a natural lens, the intraocular lens accommodating in response to movement of the capsular sac, the intraocular lens comprising:
   an optic portion including a lens element, an intermediate layer and an actuator, the actuator disposed in contact with the lens element;
   a haptic having an interior volume coupled in fluid communication with the actuator;
   a fluid disposed in the actuator and the interior volume of the haptic; and
   a secondary deflection mechanism coupled to the lens element,
   wherein the lens element is configured to be deformed by movement of the actuator in response to movement of the first fluid between the haptic and the actuator, and
   wherein the secondary deflection mechanism is configured to further deform the lens element in response to deformation of the lens element by the actuator.

2. The intraocular lens of claim 1 wherein the secondary deflection mechanism is a portion of the lens element having a reduced thickness.

3. The intraocular lens of claim 1 wherein the secondary deflection mechanism is a flexible coupling between the lens element and the intermediate layer.

4. The intraocular lens of claim 1 wherein the secondary deflection mechanism is a fluid-mediated actuator comprising a sealed cavity between the lens element and the intermediate layer that is filled with a second fluid, and
   wherein deformation of the lens element and movement of the actuator redistributes the second fluid within the sealed cavity which further deforms the lens element.

5. The intraocular lens of claim 4 wherein the first fluid and the second fluid have approximately the same refractive index.

6. The intraocular lens of claim 4 wherein the lens element and the actuator are configured such that the volume of a peripheral portion of the sealed cavity decreases and the volume of a central portion of the sealed cavity increases when the first fluid is transferred from the haptic to the actuator.

7. The intraocular lens of claim 1 further comprising a backstop coupled to at least a portion of the haptic.

8. The intraocular lens of claim 1 further comprising a support member that extends further radially outward than the haptic.

9. The intraocular lens of claim 1 wherein the actuator includes a rolling undulation.

10. The intraocular lens of claim 1 wherein the actuator includes a bellows.

11. The intraocular lens of claim 1 wherein the intermediate layer and the actuator are monolithic.

12. The intraocular lens of claim 1 wherein the intermediate layer and the actuator are separate components coupled together.

13. The intraocular lens of claim 4 wherein the lens element and the intermediate layer are sealed such that relative motion adjacent the seal is permitted.

14. The intraocular lens of claim 1 wherein the lens element is deformed to an aspheric configuration by the actuator and secondary deflection mechanism.

15. An intraocular lens configured for implantation in a capsule following extraction of a natural lens, the intraocular lens accommodating in response to shape changes of the patient's lens capsule, the intraocular lens comprising:
   an optic portion including a lens element, an actuator and a sealed fluid cavity adjacent at least a portion of the lens element;
   a haptic having an interior volume coupled in fluid communication with the actuator, and a capsule wall contacting portion;
   a first fluid disposed in the actuator and the interior volume of the haptic; and
   a second fluid disposed in the sealed fluid cavity,
   wherein the actuator is coupled with the lens element such that shape changes of the patient's lens capsule displaces fluid between the interior volume of the haptic and the actuator to change a deflection of the lens element, and
   wherein deflection of the lens element causes the second fluid to redistribute within the sealed fluid cavity to alter the deflection of the lens element.

16. The intraocular lens of claim 15 further comprising a backstop coupled to at least a portion of the haptic.

17. The intraocular lens of claim 15 further comprising a support member that extends further radially outward than the haptic.

18. The intraocular lens of claim 17 wherein the support member is a wire that circumscribes and is radially spaced from the haptic.

19. The intraocular lens of claim 17 wherein the support member is a tab that extends radially outward from a portion of the haptic.

20. The intraocular lens of claim 15 wherein the support member is integrated into the haptic.

21. The intraocular lens of claim 15 wherein the actuator includes a rolling undulation.

22. The intraocular lens of claim 15 wherein the actuator includes a bellows.

23. The intraocular lens of claim 15 wherein a plurality of sealed fluid cavities are included adjacent the lens element.

24. The intraocular lens of claim 15 further comprising a coating disposed on the inner surfaces of the sealed fluid cavity that is configured to prevent diffusion of the second fluid out of the sealed fluid cavity.

25. An intraocular lens configured for implantation in a capsular sac following extraction of a natural lens, the intraocular lens accommodating in response to movement of the capsular sac, the intraocular lens comprising:
   an optic portion including a lens element and an actuator;

a haptic having an interior volume coupled in fluid communication with the actuator;

a fluid disposed in the actuator and the interior volume of the haptic; and a secondary deflection mechanism coupled to the lens element, wherein the actuator is configured to deform the lens element in response to movement of the fluid between the haptic and the actuator, and wherein the secondary deflection mechanism is configured to further deform the lens element to an aspheric shape in response to deformation of the lens element by the actuator.

26. The intraocular lens of claim 25 wherein the secondary deflection mechanism is a portion of the lens element having a reduced thickness.

27. The intraocular lens of claim 25 wherein the secondary deflection mechanism is a flexible coupling between the lens element and the intermediate layer.

28. The intraocular lens of claim 25 wherein the secondary deflection mechanism is a fluid-mediated actuator comprising a sealed cavity between the lens element and the intermediate later that is filled with a second fluid, and wherein deformation of the lens element and movement of the actuator redistributes the second fluid within the sealed cavity which further deforms the lens element.

* * * * *

UNITED STATES PATENT AND TRADEMARK OFFICE
CERTIFICATE OF CORRECTION

PATENT NO.      : 7,637,947 B2
APPLICATION NO. : 11/646913
DATED           : December 29, 2009
INVENTOR(S)     : Smith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 432 days.

Signed and Sealed this

Ninth Day of November, 2010

David J. Kappos
*Director of the United States Patent and Trademark Office*